(12) United States Patent
Toshima et al.

(10) Patent No.: US 7,429,109 B2
(45) Date of Patent: Sep. 30, 2008

(54) OPTOMETRIC APPARATUS AND LENS POWER DETERMINATION METHOD

(75) Inventors: Akio Toshima, Akashi (JP); Takehiko Yoshida, Higashiosaka (JP)

(73) Assignee: Vision Optic Co., Ltd., Osaka (JP)

( * ) Notice: Subject to any disclaimer, the term of this patent is extended or adjusted under 35 U.S.C. 154(b) by 133 days.

(21) Appl. No.: 10/531,958

(22) PCT Filed: Aug. 26, 2003

(86) PCT No.: PCT/JP03/10733

§ 371 (c)(1), (2), (4) Date: Jan. 6, 2006

(87) PCT Pub. No.: WO2004/034893

PCT Pub. Date: Apr. 29, 2004

(65) Prior Publication Data

US 2006/0152675 A1  Jul. 13, 2006

(30) Foreign Application Priority Data

Oct. 21, 2002 (JP) ............................. 2002-306419

(51) Int. Cl.
*A61B 3/02* (2006.01)
*A61B 3/00* (2006.01)

(52) U.S. Cl. .................... 351/239; 351/223; 351/246

(58) Field of Classification Search .............. 351/239, 351/222, 223, 224, 227, 240, 241, 246, 205, 351/206, 159, 212; 600/558
See application file for complete search history.

(56) References Cited

U.S. PATENT DOCUMENTS 5,675,399 A    10/1997   Kohayakawa
5,929,972 A *   7/1999   Hutchinson .................. 351/237
6,742,895 B2 *  6/2004   Robin ......................... 351/246
7,267,439 B2 *  9/2007   Toshima et al. .............. 351/223

FOREIGN PATENT DOCUMENTS

JP    56-018212    2/1981

(Continued)

*Primary Examiner*—Ricky Mack
*Assistant Examiner*—Tuyen Tra
(74) *Attorney, Agent, or Firm*—Keating & Bennett, LLP

(57) ABSTRACT

An optometric apparatus and an optometric method which perform an accurate eye examination on people who have a wide range of refractive powers with astigmatism, myopia or hyperopia, and which are also applicable especially to those with mixed astigmatism are provided. The apparatus performs a subjective eye examination by prompting a subject to view test symbols displayed on a computer screen by one of the right and left eyes at a time. The system includes astigmatic axis angle determination means which displays test symbols for determining an astigmatic axis angle and then determines the astigmatic axis angle, hyperopia and myopia determination means which displays test symbols for determining hyperopia or myopia in two orthogonal orientations selected based on the determined astigmatic axis angle, and determines hyperopia or myopia at the astigmatic axis angle and at an angle orthogonal thereto, and refractive power determination means which displays test symbols for determining a refractive power in two orthogonal orientations selected based on the determined astigmatic axis angle and determines a refractive power at the astigmatic axis angle and at an angle orthogonal thereto.

10 Claims, 20 Drawing Sheets

FOREIGN PATENT DOCUMENTS

| | | |
|---|---|---|
| JP | 07-299034 | 11/1995 |
| JP | 11-290273 | 10/1999 |
| JP | 2000-041943 | 2/2000 |
| JP | 2000-107129 | 4/2000 |
| JP | 2001-286442 | 10/2001 |
| JP | 2002-083156 | 3/2002 |

* cited by examiner

Astigmatic axis measurement chart 1

"One viewed with higher contrast"   "Two or more viewed with higher contrast"   "All viewed equally"

Astigmatic axis measurement chart 2

"One viewed with higher contrast"   "Two or more viewed with higher contrast"   "All viewed equally"

"None viewed with 3 lines"

"None viewed with 3 lines"

"None viewed with 3 lines"

OPTOMETRIC APPARATUS AND LENS POWER DETERMINATION METHOD

BACKGROUND OF THE INVENTION

1. Field of the Invention

The present invention relates to an optometric apparatus and a lens power determination method to perform a subjective eye examination by prompting a subject to view test symbols displayed on a display means using one of the right and left eyes at a time. More particularly, the present invention relates to an optometric apparatus and a lens power determination method which are suitable for eye examinations performed to determine lens powers, e.g., in order to sell eyeglasses or contact lenses over the Internet.

2. Description of the Related Art

Conventionally, to determine the refractive power of eyeglasses or contact lenses, a conventional method used an auto-refractometer to objectively determine the refractive coefficient of the eyeball and then the subject actually wore ready-made corrective lenses in order to test the subject's visual acuity.

However, such an auto-refractometer is very expensive and requires expert knowledge to operate. Additionally, to actually wear corrective lenses when testing visual acuity, the subject had to visit an ophthalmologist or to go to an eyeglass shop for an eye examination, where various types of corrective lenses were available. Thus, it was difficult to order eyeglasses or contact lenses at shops or at home where no such facilities were available.

Recently, with the advancement of computers and network technologies, a system is being developed which allows the user to perform a subjective eye examination at shops or at home where no facilities, such as an auto-refractometer or corrective lenses are available (e.g., A remote visual acuity determination system disclosed in Japanese Patent Laid-Open Publication No. 2001-286442).

Such a conventional system displays test symbols for determining visual acuity or "Landoldt rings", as shown in FIG. 21, to the subject in various sizes on a computer screen. The system then allows the subject to select the smallest viewable test symbol for each of the right and left eyes, thereby determining the subject's visual acuity. In addition, for subjects having astigmatism, the system displays a rotating Landoldt ring for the subject to determine the orientation in which the opening or break appears closed. The system also displays a test symbol, shown in FIG. 22, for determining an astigmatic axis on a computer screen, and the subject selects the orientation in which the subject is viewed with the highest contrast (or most clearly or most sharpest) for each of the right and left eyes, thereby determining the subject's astigmatic axis. Then, the visual acuity is determined based on the test symbols for determining visual acuity at the determined astigmatic axis and in an orientation orthogonal thereto.

Alternatively, the system may be used by an unlimited number of people via the Internet, so some of the subjects may have hyperopia. However, the conventional optometric device simply provided test symbols in various sizes for the subject to select the smallest viewable test symbol. Thus, the difference between myopia and hyperopia cannot be distinguished, which may provide misleading eye examination results.

In particular, since the eye examination performed on a computer screen requires the entry of results of viewing by the subject using a mouse or the like, the distance between the subject's eye and the test symbol is restricted within a specific range. Thus, it is difficult to distinguish between hyperopia and myopia using only the test symbols for determining visual acuity.

Furthermore, although some subjects with astigmatism may have mixed astigmatism which causes one of the major and minor axes to exhibit myopia and the other to exhibit hyperopia, the conventional optometric device cannot be applied to these subjects.

SUMMARY OF THE INVENTION

In order to overcome the problems described above, preferred embodiments of the present invention provide an optometric apparatus and a lens power determination method which can perform accurate eye examinations on those who have astigmatism, myopia, and hyperopia and a wide range of refractive powers, and which can also be applied particularly to those with mixed astigmatism.

An optometric apparatus according to preferred embodiments of the present invention performs a subjective eye examination by prompting a subject to view test symbols displayed on a display means using one of the right and left eyes at a time and then obtaining the results of viewing by the subject. The optometric apparatus includes astigmatic axis angle determination means for displaying test symbols for determining an astigmatic axis angle and then obtaining a result of viewing by the subject to determine the astigmatic axis angle, hyperopia and myopia determination means for displaying test symbols for determining hyperopia or myopia in two orthogonal orientations selected in accordance with the determined astigmatic axis angle, and then obtaining a result of viewing by the subject to determine hyperopia or myopia at the astigmatic axis angle determined and at an angle orthogonal thereto, and refractive power determination means for displaying test symbols for determining a refractive power in two orthogonal orientations selected in accordance with the determined astigmatic axis angle, and then obtaining a result of viewing by the subject to determine refractive powers at the astigmatic axis angle determined and at an angle orthogonal thereto.

The present invention includes the hyperopia and myopia determination means which determines whether the subject has hyperopic eyes or myopic eyes, thereby providing an accurate eye examination even for subjects having hyperopia.

Furthermore, the optometric apparatus also has a function to determine the subject's astigmatic axis by the astigmatic axis angle determination means, a function to individually determine hyperopia or myopia in two orthogonal orientations selected in accordance with the astigmatic axis by the hyperopia and myopia determination means, and a function to determine a refractive power in two orthogonal orientations selected in accordance with the astigmatic axis by the refractive power determination means. Thus, it is possible to perform an eye examination even on subjects with mixed astigmatism.

The astigmatic axis angle determination means preferably includes means for displaying an astigmatic axis determination chart which includes four test symbols, each having multiple straight lines arranged in parallel at angles of about 45 degrees, about 90 degrees, about 135 degrees, and about 180 degrees, respectively, means for prompting the subject to select any test symbol viewed with greater contrast (or more clearly or more sharply than others) in the displayed astigmatic axis determination chart, and means for determining an astigmatic axis angle in accordance with the test symbol selected in the astigmatic axis determination chart.

The optometric apparatus for providing a subjective eye examination by allowing the subject to view a test symbol displayed on the display means requires the subject to view and determine the test symbol displayed on the display means by himself. However, in the determination of astigmatic axis, different distances between the test symbol and the eye of the subject provide subtly different views. Thus, it has been difficult for ordinary people to use a test symbol having one straight line disposed radially or a rotated test symbol of two straight lines to determine astigmatic axes.

The present invention allows the astigmatic axis angle determination means to display an astigmatic axis determination chart including a combination of the test symbols which have groups of multiple lines arranged in parallel at approximately 45 degree intervals in four limited orientations. The system then prompts the subject to select any test symbol viewed with greater contrast, thereby facilitating selection of astigmatic axes even by ordinary people, and thus preventing erroneous determinations.

The astigmatic axis angle determination means preferably includes means for displaying a first astigmatic axis determination chart which includes four test symbols each having multiple straight lines arranged in parallel in four orientations at angles of about 45 degrees, about 90 degrees, about 135 degrees, and about 180 degrees, respectively, means for prompting the subject to select any test symbol viewed with greater contrast in the first astigmatic axis determination chart displayed, means for displaying a second astigmatic axis determination chart which includes four test symbols each having multiple straight lines arranged in parallel in four orientations approximately intermediate to the aforementioned four orientations, means for prompting the subject to select any test symbol viewed with greater contrast in the second astigmatic axis determination chart displayed, and means for determining an astigmatic axis angle in accordance with the test symbol selected in the first astigmatic axis determination chart and the test symbol selected in the second astigmatic axis determination chart.

The present invention allows the astigmatic axis angle determination means to display an astigmatic axis determination chart including a combination of the test symbols which have groups of multiple lines arranged in parallel at approximately 45 degree intervals in four limited orientations. The system then prompts the subject to select any test symbol viewed with greater contrast, thereby facilitating selection of astigmatic axes even by ordinary people, and thus preventing erroneous determinations.

Furthermore, the astigmatic axis angle determination means also displays an astigmatic axis determination chart which includes a combination of test symbols disposed in four orientations approximately intermediate to about 45 degrees, about 90 degrees, about 135 degrees, and about 180 degrees, and then prompts the subject to select any test symbol viewed with greater contrast. The astigmatic axis angle is thus determined in accordance with the test symbols selected in the two astigmatic axis determination charts. This allows for determining the astigmatic axis at a further intermediate angle by calculation based on the angles of the test symbols selected in the two astigmatic axis determination charts. Thus, the astigmatic axis angle can be determined substantially with twice the resolution for the test symbols displayed in a total of eight orientations.

The astigmatic axis angle determination means preferably includes means for displaying a first astigmatic axis determination chart which includes four test symbols having multiple straight lines arranged in parallel in four orientations at angles of about 45 degrees, about 90 degrees, about 135 degrees, and about 180 degrees, respectively, means for prompting the subject to select any test symbol viewed with greater contrast in the displayed first astigmatic axis determination chart, means for displaying a second astigmatic axis determination chart which includes four test symbols having multiple straight lines arranged in parallel in four orientations approximately intermediate to the aforementioned four orientations, means for prompting the subject to select any test symbol viewed with greater contrast in the displayed second astigmatic axis determination chart, means for displaying a third astigmatic axis determination chart which includes the test symbol selected by the subject in the first astigmatic axis determination chart and the test symbol selected by the subject in the second astigmatic axis determination chart, means for prompting the subject to select any test symbol viewed with greater contrast in the displayed third astigmatic axis determination chart, means for determining an astigmatic axis angle in accordance with the test symbol selected in the first astigmatic axis determination chart, the test symbol selected in the second astigmatic axis determination chart, and the test symbol selected in the third astigmatic axis determination chart.

The present invention allows the astigmatic axis angle determination means to display an astigmatic axis determination chart including a combination of the test symbols which include groups of multiple lines arranged in parallel at approximately 45 degree intervals in four limited orientations. The system then prompts the subject to select any test symbol viewed with greater contrast, thereby facilitating determination of astigmatic axes even by ordinary people, and thus preventing erroneous determinations.

Furthermore, the astigmatic axis angle determination means also displays the second astigmatic axis determination chart which includes a combination of test symbols disposed in four orientations approximately intermediate to about 45 degrees, about 90 degrees, about 135 degrees, and about 180 degrees, and then prompts the subject to select any test symbol viewed with greater contrast. Additionally, the astigmatic axis angle determination means also displays the third astigmatic axis determination chart which includes a combination of the test symbols selected in the two astigmatic axis determination charts, and then prompts the subject to select any test symbol viewed with greater contrast. Thus, the astigmatic axis angle is determined in accordance with the test symbols selected in the three astigmatic axis determination charts. This allows for determining the astigmatic axis at an intermediate angle by calculation based on the angles of the test symbols selected in the three astigmatic axis determination charts. Thus, the astigmatic axis angle can be determined with approximately twice the resolution for the test symbols displayed in a total of eight orientations.

Furthermore, even when the subject has selected some test symbols by mistake, the test symbols selected in the three astigmatic axis determination charts can be checked with each other to provide a correct determination. Thus, it is possible to determine the astigmatic axis angle of the subject with greater accuracy.

The hyperopia and myopia determination means preferably includes means for displaying a first hyperopia and myopia determination chart having a red-based color background area and a blue-based color background area, in both of the areas, black-based color straight lines are drawn in one of the two selected orthogonal orientations, means for prompting the subject to select the area which provides a clearer appearance of the straight lines in the displayed first hyperopia and myopia determination chart displayed, means for displaying a second hyperopia and myopia determination chart having a red-based color background area and a blue-based color background area, in both of the areas, black-based color straight lines are drawn in the other of the two selected orthogonal orientations, means for prompting the subject to select the area which provides a clearer appearance of the straight lines in the second hyperopia and myopia determination chart displayed, means for determining hyperopia and myopia at the astigmatic axis angle determined and at an angle orthogonal thereto in accordance with a result selected in the first hyperopia and myopia determination chart and a result selected in the second hyperopia and myopia determination chart.

The present invention allows the hyperopia and myopia determination means to use a test symbol having black-based color straight lines drawn in both of the areas in either one of the two orthogonal orientations selected in accordance with the astigmatic axis angle determined by the astigmatic axis angle determination means. The hyperopia and myopia determination means displays the first hyperopia and myopia determination chart having straight lines drawn in both of the areas in one of the two orientations and the second hyperopia and myopia determination chart having straight lines in both of the areas in the other of the two orthogonal orientations. The hyperopia and myopia determination means prompts the subject to select the area which provides a clearer appearance of the straight lines in each of the hyperopia and myopia determination charts, thereby determining hyperopia or myopia at the astigmatic axis angle of the subject and at an angle orthogonal thereto.

This is achieved by a phenomenon that the red-based color area provides a clearer appearance to a myopic eye whereas the blue-based color area provides a clearer appearance to a hyperopic eye. This phenomenon results from the fact that when the red-based and blue-based color areas are viewed by the human eye at the same time, chromatic aberration causes the red-based color to be focused rearward and the blue-based color frontward. Accordingly, the subject is only required to determine, and thus easily determines which area provides a clearer appearance.

Furthermore, this hyperopia and myopia determination chart also indicates directive test symbols having straight lines which are oriented in two orthogonal orientations selected in accordance with the astigmatic axis angle determined by the astigmatic axis angle determination means and which are drawn in the two color areas exhibiting chromatic aberration. Thus, it is possible to detect the dependency of hyperopia and myopia on angle. This allows for determining hyperopia and myopia independently at the astigmatic axis angle of the subject and at an angle orthogonal thereto, respectively. This is also applicable to subjects with mixed astigmatism.

The hyperopia and myopia determination means preferably includes means for displaying a first hyperopia and myopia determination chart having a red-based color background area and a blue-based color background area, in both of the areas black-based color straight lines are drawn in one of the two selected orthogonal orientations, means for prompting the subject to select the area which provides a clearer appearance of the straight lines in the first hyperopia and myopia determination chart displayed, means for displaying a second hyperopia and myopia determination chart having a red-based color background area and a blue-based color background area, in both of the areas black-based color straight lines are drawn in the other of the two selected orthogonal orientations, means for prompting the subject to select the area which provides a clearer appearance of the straight lines in the second hyperopia and myopia determination chart displayed, means for displaying a third hyperopia and myopia determination chart having a red-based color background area in which black-based color straight lines are drawn in the one of the two selected orthogonal orientations and a blue-based color background area in which black-based color straight lines are drawn in the other of the two selected orthogonal orientations, means for prompting the subject to select the area which provides a clearer appearance of the straight lines in the third hyperopia and myopia determination chart displayed, means for displaying a fourth hyperopia and myopia determination chart having a red-based color background area in which black-based color straight lines are drawn in the other of the two selected orthogonal orientations and a blue-based color background area in which black-based color straight lines are drawn in the one of the two selected orthogonal orientations, means for prompting the subject to select the area which provides a clearer appearance of the straight lines in the fourth hyperopia and myopia determination chart displayed, and means for determining hyperopia and myopia at the determined astigmatic axis angle and at an angle orthogonal thereto in accordance with a result selected in the first hyperopia and myopia determination chart, a result selected in the second hyperopia and myopia determination chart, a result selected in the third hyperopia and myopia determination chart, and a result selected in the fourth hyperopia and myopia determination chart.

The present invention allows the hyperopia and myopia determination means to use a test symbol which has a red-based color background area and a blue-based color background area, in both of the areas black-based color straight lines are drawn in either one of the two orthogonal orientations selected in accordance with the astigmatic axis angle determined by the astigmatic axis angle determination means. The hyperopia and myopia determination means displays the first hyperopia and myopia determination chart having straight lines drawn in both of the areas in one of the two orientations, the second hyperopia and myopia determination chart having straight lines in both of the areas in the other of the two orthogonal orientations, the third hyperopia and myopia determination chart having straight lines which are drawn in the one of the two orientations in one area and which are drawn in the other of the two orientations in the other area, and the fourth hyperopia and myopia determination chart having straight lines which are drawn in the other of the two orientations in one area and which are drawn in the one of the two orientations in the other area. The hyperopia and myopia determination means prompts the subject to select the area which provides a clearer appearance of the straight lines in each of the hyperopia and myopia determination charts, thereby determining the hyperopia or myopia at the astigmatic axis angle of the subject and at an angle orthogonal thereto.

This is achieved by a phenomenon that the red-based color area provides a clearer appearance to a myopic eye whereas the blue-based color area provides a clearer appearance to a hyperopic eye. This phenomenon results from the fact that when the red-based color area and the blue-based color area are viewed by the human eye at the same time, chromatic aberration causes the red-based color to be focused rearward and the blue-based color to be focused frontward. Accordingly, the subject is only required to determine and thus easily determines which area provides a clearer appearance.

Furthermore, this hyperopia and myopia determination chart also indicates directive test symbols having straight lines which are oriented in two orthogonal orientations selected in accordance with the astigmatic axis angle determined by the astigmatic axis angle determination means and which are drawn in the two color areas exhibiting chromatic aberration. Thus, it is possible to detect the dependency of hyperopia and myopia on angle. This allows for determining hyperopia and myopia independently at the astigmatic axis angle of the subject and at an angle orthogonal thereto, respectively. This is also applicable to subjects with mixed astigmatism.

Furthermore, hyperopia and myopia are to be determined using the third hyperopia and myopia determination chart and the fourth hyperopia and myopia determination chart, in each of which straight lines are drawn in each of the areas in two different orientations in addition to the first hyperopia and myopia determination chart and the second hyperopia and myopia determination chart, in each of which straight lines are drawn in both of the areas in either one of two orientations. Accordingly, even in the presence of some erroneous determinations made by the subject, it is possible to check the results selected in the four charts with each other, thereby making the correct determination. This allows for determining hyperopia and myopia at the astigmatic axis angle of the subject and at an angle orthogonal thereto with greater accuracy.

When the subject has selected either the "red-based color area" or "Viewed equally" but not the "blue-based color area" in both of the first hyperopia and myopia determination chart and the second hyperopia and myopia determination chart, the subject is considered to have no hyperopic factor, and thus determinations to be made using the third hyperopia and myopia determination chart and the fourth hyperopia and myopia determination chart may be omitted. This makes it possible to determine hyperopia and myopia more efficiently.

The hyperopia and myopia determination means preferably includes the hyperopia and myopia determination chart in which the blue-based color area has a lower brightness than that of the red-based color area.

Typically, a computer screen is often viewed at a subject's reach (about 60 cm to about 70 cm). If a hyperopia and myopia determination chart using two colors, or the red-based color and blue-based color, are displayed at this distance for determinations by a subject, a subject with emmetropia having a relatively good visual acuity or weak myopia would sometimes erroneously select the blue-based color area because the area is focused behind the retina due to the relatively short distance to the screen.

Since this invention provides the hyperopia and myopia determination chart in which the blue-based color area has a lower brightness than that of the red-based color area, even when the computer screen is viewed at a subject's reach, a subject with emmetropia or weak myopia is prevented from erroneously selecting the blue-based color area. This allows for determining hyperopia and myopia with increased accuracy.

The hyperopia and myopia determination means preferably limits the time of displaying each of the hyperopia and myopia determination charts.

The present invention limits the time of displaying each hyperopia and myopia determination chart, thereby allowing the subject to make a determination before the accommodation of the eye becomes significant. In particular, this is effective when the subject moves closer to the test symbol until it is viewed clearly for determination with a test symbol maintained at a specific size. This prevents an erroneous determination which occurs because the subject intensively accommodates the eyes in an attempt to properly adjust the focal length.

The refractive power determination means preferably includes means for displaying a refractive power determination chart in which test symbols having a desired number of straight lines arranged in parallel in the two selected orthogonal orientations are varied in size in a stepwise manner, means for prompting the subject to select the smallest viewable test symbol in the displayed refractive power determination chart, and means for determining refractive powers at the determined astigmatic axis angle and at an angle orthogonal thereto in accordance with the test symbol selected in the refractive power determination chart.

The present invention allows the refractive power determination means to use the refractive power determination chart in which test symbols having a desired number of straight lines arranged in parallel in the two orthogonal orientations selected in accordance with the determined astigmatic axis angle by the astigmatic axis angle determination means are varied in size in a stepwise manner corresponding to refractive powers. The refractive power determination means then prompts the subject to select the smallest test symbol in which the number of straight lines can be correctly recognized. Accordingly, when compared to the rotating Landoldt ring having a partial break for determination, it is possible to provide test symbols in a larger number of steps in size. This makes it possible to increase resolution in determination of refractive powers, thereby accurately determining the refractive powers at the astigmatic axis angle of the subject and the angle orthogonal thereto.

All the test symbols varied in size in a stepwise manner may be included in one refractive power determination chart, in which the smallest viewable test symbol may be selected. The test symbols may also be divided into a plurality of classes according to their size to successively display the charts including their respective classes of test symbols, thereby allowing the smallest viewable test symbol to be selected. Alternatively, only one test symbol may be included in one chart, which is then displayed successively in order of increasing size, thereby allowing the smallest viewable test symbol to be selected.

The refractive power determination means preferably includes means for sequentially displaying a plurality of refractive power determination charts which have a combination of test symbols having a desired number of straight lines drawn in parallel in the two selected orthogonal orientations in which the step difference in size is two or more, means for prompting the subject to select the smallest viewable test symbol in each of the displayed refractive power determination charts, and means for determining refractive powers at the determined astigmatic axis angle and at an angle orthogonal thereto in accordance with the test symbols selected in each of the refractive power determination charts.

The present invention allows the refractive power determination means to sequentially display a plurality of refractive power determination charts which have a combination of test symbols in which the step difference in size is two or more corresponding to refractive powers. Here, the test symbols have a desired number of straight lines drawn in parallel in the two orthogonal orientations selected in accordance with the astigmatic axis angle determined by the astigmatic axis angle determination means. The refractive power determination means then prompts the subject to select the smallest test symbol in which the number of straight lines can be correctly recognized in each refractive power determination chart. Accordingly, when compared to the conventional rotating Landoldt ring having a partial break for determination, it is possible to provide test symbols in a larger number of steps in size. This makes it possible to increase resolution of the determination of refractive powers, thereby more accurately determining the refractive powers at the astigmatic axis angle of the subject and the angle orthogonal thereto.

Since the refractive power determination charts which have a combination of test symbols in which the step difference in size is two or more are used, the subject does not have to make a subtle determination to select the smallest viewable test symbol among test symbols having a small step difference in size, thereby facilitating the selection of the smallest viewable test symbol.

Furthermore, since determinations in a plurality of refractive power determination charts are combined to determine the smallest viewable test symbol, even when some erroneous determinations are made by the subject due to pseudo-resolution, it is possible to correctly determine refractive powers by checking the determinations with each other. This allows for determining the refractive powers at the astigmatic axis angle of the subject and at an angle orthogonal thereto with increased accuracy.

In particular, it is preferable to use three refractive power determination charts in which the step difference in size of the test symbols is three. This allows the subject to easily select the smallest viewable test symbol and determine the refractive powers with accuracy through the three determinations.

The refractive power determination chart preferably includes side zones on both outside ends of a widthwise direction of the desired number of straight lines drawn, the side zones having a width about 0.5 to about 2.0 times the width of the straight lines and a specific contrast against the straight lines.

The present invention provides the refractive power determination chart with the side zones of a desired width on both outside ends of a widthwise direction of the desired number of straight lines drawn, which have a specific contrast against the straight lines. Accordingly, in the presence of pseudo-resolution, the straight lines appearing in the side zones provide a distinguishable appearance in a desired contrast against the background, allowing the subject to readily determine the presence of pseudo-resolution.

In the absence of the side zones, it is difficult to identify the viewable limit because when viewed, test symbols of smaller sizes beyond the viewable test symbol size become gradually defocused. However, the presence of the side zones causes the straight lines, areas between the lines and side zones to become jumbled while being defocused. Thus, this makes it easier to identify the viewable limit, thereby allowing for selection of the smallest viewable test symbol more precisely.

It is thus possible to determine the refractive powers at the astigmatic axis angle of the subject and at an angle orthogonal thereto with greater accuracy.

The side zones in the refractive power determination chart are preferably different in color from areas between the straight lines and equal to or greater than the areas between the straight lines in brightness.

The present invention provides the refractive power determination chart in which the side zones are different in color from the areas between the straight lines and equal to or greater than the areas between the straight lines in brightness. This allows the subject to readily determine the presence of pseudo-resolution and select the smallest viewable test symbol more precisely. Thus, it is possible to determine the refractive powers at the astigmatic axis angle of the subject and at an angle orthogonal thereto with increased accuracy.

As used herein, the "brightness" refers to the subjective brightness when the light is transmitted into the eye. For example, as a measure of brightness for comparison, it is possible to use Y ($Y=0.299R+0.587G+0.114B$) in the YCC representation or V ($V=R+G+B$) in the HSV representation.

The refractive power determination chart preferably includes the straight lines in a black-based color, the areas between the straight lines in a green-based color, and the side zones in a yellow-based color.

The present invention provides the refractive power determination chart which has the straight lines arranged in a black-based color, the areas between the straight lines arranged in a green-based color, and the side zones arranged in a yellow-based color. As a result of experiments conducted on various combinations of colors, it was determined that this combination provided the most-easy-to-see appearance to subjects and allows the subjects to make precise determinations.

The refractive power determination means preferably includes far refractive power determination means for prompting the subject to view test symbols at a far distance from the display means and select the smallest viewable test symbol, near refractive power determination means for prompting the subject to view test symbols at a close distance to the display means and select the smallest viewable test symbol, and means for determining the refractive powers at the determined astigmatic axis angle and at an angle orthogonal thereto in accordance with the test symbol selected in the far refractive power determination means and the test symbol selected in the near refractive power determination means.

Typically, a computer screen is often viewed at a subject's reach (about 60 cm to about 70 cm). However, some people with hyperopia or presbyopia are at the range of accommodation at this distance because it is farther than the near point distance, thus not being able to determine their refractive power.

The present invention allows the refractive power determination means to include the far refractive power determination means for prompting test symbols to be viewed at a far distance from the display means for determination of refractive powers, and the near refractive power determination means for determining refractive powers at a near distance to the display means. The refractive power determination means has a function to determine the refractive powers at the astigmatic axis angle and at an angle orthogonal thereto in accordance with the test symbol selected in the far refractive power determination means and the test symbol selected in the near refractive power determination means.

Accordingly, the refractive power of a subject even with hyperopia or presbyopia, who is within the range of accommodation in the far refractive power determination means, can be determined.

Furthermore, when the hyperopia and myopia determination means could not determine hyperopia and myopia, it is possible to use the test symbol selected in the far refractive power determination and the test symbol selected in the near refractive power determination to determine hyperopia and myopia and calculate the refractive power at the astigmatic axis angle of the subject and at an angle orthogonal thereto. For example, a difference in size between the test symbols selected in the far refractive power determination and the near refractive power determination may be obtained. If the difference is positive and equal to or greater than a specific value (i.e., a near test symbol provides a clearer appearance), the subject may be determined to have myopia. Otherwise, if the difference is negative and equal to or less than a specific value (i.e., a far test symbol provides a clearer appearance), the subject may be determined to have hyperopia. Alternatively, a difference in size between the test symbols selected in the far refractive power determinations in two orthogonal orientations and a difference in size between the test symbols selected in the near refractive power determinations in two orthogonal orientations may be obtained. If the differences are equal to each other in sign and the former is greater than the latter, their average may be determined as an astigmatic refractive power.

On the other hand, even when hyperopia and myopia have been determined in the hyperopia and myopia determination means, the test symbol selected in the far refractive power determination and the test symbol selected in the near refractive power determination may be checked with each other, thereby correcting any errors made by the subject. Moreover, in the determination of refractive powers, both the test symbol selected in the far refractive power determination and the test symbol selected in near refractive power determination may be used to determine the refractive power by calculation. This allows for more accurate determinations of hyperopia and myopia and for the refractive power determination at the astigmatic axis angle of the subject and at an angle orthogonal thereto.

Typically, a computer screen is often viewed at about a subject's reach, and most people with hyperopia or presbyopia have a near point distance of about 30 cm or more. Accordingly, the far refractive power determination may be made, e.g., at a subject's reach (about 60 cm to about 70 cm) to the display means, whereas the near refractive power determination may be made, e.g., at a distance of an A4-size piece of paper (about 30 cm) disposed longitudinally between the eye of the subject and the display means.

The near refractive power determination means is preferably performed on a subject of a predetermined age or older, determined to have hyperopia by the hyperopia and myopia determination means, and on a subject whose determination is suspended in the hyperopia and myopia determination means.

The present invention provides the refractive power determination means in which the near refractive power determination is to be made only on subjects of a specific age or older with hyperopia and those to whom no determination is made in the hyperopia and myopia determination means. Those with good eyes and myopia can obtain a good result only by the far refractive power determination, and thus the near refractive power determination is eliminated.

The near refractive power determination is made only when required, thereby making it possible to efficiently determine the refractive power of the subject.

The refractive power determination means preferably includes means for displaying a refractive power determination chart having test symbols varied in size in a stepwise manner, each of the test symbols having a line group area with red-based color straight lines and blue-based color straight lines of a uniform width drawn alternately in the two selected orthogonal orientations, and a reference color area of the same color as either one of the straight lines in the line group area, means for prompting the subject to select the smallest test symbol in the refractive power determination chart displayed in which any straight lines in the line group area provide an appearance of the same color as that of the reference color area, and means for determining the refractive powers at the determined astigmatic axis angle and at an angle orthogonal thereto in accordance with the test symbol selected in the refractive power determination chart.

The present invention includes a refractive power determination chart which includes test symbols varied in size in a stepwise manner according to refractive powers to determine refractive powers. The test symbol includes the line group area with red-based color straight lines and blue-based color straight lines drawn alternately. The test symbol also includes the reference color area of the same color as either one of the straight lines in the line group area.

With this configuration, refractive powers are determined using the following fact. That is, when the subject views the test symbols having straight lines drawn in two colors, such a test symbol as having the straight lines spaced at larger intervals than the resolution of the eye corresponding to its visual acuity provides an appearance of two properly separated colors. However, such a test symbol having the straight lines spaced at smaller intervals than the resolution of the eye corresponding to its visual acuity provides an appearance of the two colors being mixed up.

This allows the subject to intuitively determine the smallest viewable test symbol while alleviating the problem that pseudo-resolution causes the subject to incorrectly determine the number of straight lines.

The colors to be used are not necessarily limited to the red-based color and the blue-based color. Any combination of colors may also be used as long as the colors being mixed up can be properly recognized by the subject.

Here, the test symbols varying in size in a stepwise manner corresponding to refractive powers were used to enable the subject to select the smallest viewable test symbol. However, it is also acceptable to use a test symbol having two colors placed radially alternately, and thereby determine refractive powers in accordance with the distance from the center to the position nearest to the center at which the two colors can be separately recognized. In this case, since the refractive powers corresponding to orientations can also be determined, the astigmatic axis angle determination and refractive power determination may be performed simultaneously. Furthermore, for example, the combination of colors to be mixed in longer wavelength and that in shorter wavelength may be combined together such that the astigmatic axis determination, the hyperopia and myopia determination, and the refractive power determination may be performed simultaneously. This makes it possible to perform an eye examination in a very efficient manner.

The refractive power determination means preferably includes means for sequentially displaying a plurality of refractive power determination charts having a combination of test symbols having a line group area with red-based color straight lines and blue-based color straight lines of a uniform width drawn alternately in the two selected orthogonal orientations in which the step difference in size is two or more, and a reference color area of the same color as either one of the straight lines in the line group area, means for prompting the subject to select the smallest test symbol in each of the displayed refractive power determination charts in which any straight lines in the line group area provide an appearance of the same color as that of the reference color area, and means for determining the refractive powers at the determined astigmatic axis angle and at an angle orthogonal thereto in accordance with the test symbol selected in each of the refractive power determination charts.

The present invention sequentially displays a plurality of refractive power determination charts which includes test symbols in which the step difference in size is two or more corresponding to refractive powers to determine refractive powers. The refractive power determination charts have the line group area with red-based color straight lines and blue-based color straight lines drawn alternately and the reference color area of the same color as either one of the straight lines in the line group area.

In this manner, by using of a mixture of two colors, viewability is determined. This allows the subject to intuitively determine the smallest viewable test symbol while alleviating the problem that pseudo-resolution causes the subject to incorrectly determine the number of straight lines.

Since the refractive power determination charts which have a combination of test symbols in which the step difference in size is two or more are used, the subject is freed from making a subtle determination to select the smallest viewable test symbol among test symbols having a small step difference in size, thereby facilitating the selection of the smallest viewable test symbol.

Furthermore, since determinations in a plurality of refractive power determination charts are combined to determine the smallest viewable test symbol, even when some erroneous determinations are made by the subject due to pseudo-resolution, it is possible to correctly determine refractive powers by checking the determinations with each other. This allows for determining the refractive powers at the astigmatic axis angle of the subject and at an angle orthogonal thereto with increased accuracy.

In particular, it is preferable to use three refractive power determination charts in which the step difference in size of the test symbols is three. This allows the subject to easily select the smallest viewable test symbol and determine the refractive powers with accuracy through the three determinations.

The optometric apparatus according to the present invention preferably includes rough determination means including means for displaying a rough determination chart in which test symbols having no directivity are varied in size in a stepwise manner and means for prompting the subject to select the smallest viewable test symbol in the displayed rough determination chart to determine a subject's rough view, wherein the astigmatic axis angle determination means includes means for adjusting the size of each test symbol in each of the astigmatic axis determination charts to be displayed in accordance with the determined rough view.

The present invention allows the rough determination means to determine a subject's rough view using the rough determination chart, while allowing the astigmatic axis angle determination means to adjust the size of the test symbol to be displayed in accordance with the rough view. This allows the subject to determine the astigmatic axis on test symbols of suitable sizes corresponding to his own visual acuity, thereby making the determination easily.

The rough determination chart includes test symbols having no directivity. Thus, even when a subject has astigmatism, it is possible to determine the rough view independent of the astigmatic axis angle.

The optometric apparatus according to the present invention preferably includes rough determination means including means for displaying a rough determination chart in which test symbols having no directivity are varied in size in a stepwise manner and means for prompting the subject to select the smallest viewable test symbol in the displayed rough determination chart to determine a subject's rough view, wherein the hyperopia and myopia determination means includes means for adjusting the width and intervals of the straight lines drawn in each of the hyperopia and myopia determination charts to be displayed in accordance with the rough view determined.

The present invention allows the rough determination means to determine a subject's rough view using the rough determination chart, while allowing the hyperopia and myopia determination means to adjust the width and intervals of the straight lines drawn in each of the hyperopia and myopia determination chart to be displayed in accordance with the rough view determined. This allows the subject to determine hyperopia and myopia on test symbols of suitable sizes according to his own visual acuity.

In accordance with the rough view, the straight lines drawn in the hyperopia and myopia determination chart may be increased in width relative to their spacing with increasing subject's refractive powers. This can alleviate the problem that a determination is difficult because the red-based color provides a more expanded and thus more-hard-to-view straight line appearance to those with more severe myopia.

The rough determination chart uses test symbols having no directivity. Thus, even when a subject has astigmatism, it is possible to determine the rough view independent of the astigmatic axis angle.

The optometric apparatus according to the present invention preferably includes rough determination means including means for displaying a rough determination chart in which test symbols having no directivity are varied in size in a stepwise manner and means for prompting the subject to select the smallest viewable test symbol in the displayed rough determination chart to determine a subject's rough view, wherein the refractive power determination means includes means for restricting the range of size of the test symbol in the refractive power determination chart to be displayed in accordance with the determined rough view.

The present invention allows the rough determination means to determine a subject's rough view using the rough determination chart, while allowing the refractive power determination means to restrict the range of size of the test symbol used in accordance with the rough view. This reduces the time required for the eye examination and facilitates the determination by the subject, thereby making it possible to conduct the eye examination with increased accuracy.

The rough determination chart uses test symbols having no directivity. Thus, even when a subject has astigmatism, it is possible to determine the rough view independent of the astigmatic axis angle.

Preferably, in at least one of the astigmatic axis angle determination means, the hyperopia and myopia determination means, and the refractive power determination means, the subject is prompted to view a test symbol while being shielded so as not to let ambient light into the subject's eye.

The present invention allows the subject to view a test symbol while being shielded from ambient light in the subject's eye. This allows a constant illumination condition in which the subject views a test symbol, thereby providing eye examinations with increased accuracy.

Furthermore, shielding ambient light causes the subject's pupil to expand and the focal depth to be decreased, thereby facilitating the determination on the test symbol.

The manner in which ambient light is shielded may be, for example, to place an opaque tube made by rolling a newspaper or A4-size paper between the eye of the subject and the display means. Using a material of a standard specification such as newspaper or A4-size paper provides a constant distance between the eye of the subject and the test symbol displayed on the display means, thereby providing an eye examination with increased accuracy.

The optometric apparatus according to the present invention preferably includes optical eyeball model determination means for selecting a start eyeball model in accordance with the refractive power determined by the refractive power determination means and determining an optical eyeball model by verifying the model for validity at a given accommodation point of the subject, and lens power determination means for verifying the focusing capability provided when the subject wears eyeglasses or contact lenses using the optical eyeball model and determining the lens power.

The present invention allows the optical eyeball model determination means to create an optical eyeball model which simulates the eye of the subject based on the refractive power determined by the refractive power determination means. Then, using the optical eyeball model, the lens power determination means verifies the focusing capability corrected by a recommended lens to determine the lens power. This makes it possible to accurately select eyeglasses or contact lenses which are suitable to the eyes of the subject.

A lens power determination method according to this invention is a method for performing a subjective lens power determination by prompting the subject to view test symbols displayed on display means by one of the right and left eyes at a time, and then obtaining a result of viewing by the subject. The method includes the steps of displaying test symbols for determining an astigmatic axis angle and then obtaining a result of viewing by the subject to determine the astigmatic axis angle, displaying test symbols for determining hyperopia or myopia in two orthogonal orientations selected in accordance with the astigmatic axis angle determined, and then obtaining a result of viewing by the subject to determine hyperopia or myopia at the astigmatic axis angle determined and at an angle orthogonal thereto, and displaying test symbols for determining a refractive power in two orthogonal orientations selected in accordance with the astigmatic axis angle determined, and then obtaining a result of viewing by the subject to determine a refractive power at the astigmatic axis angle determined and at an angle orthogonal thereto.

The present invention includes the step of determining hyperopia and myopia to determine whether the subject has hyperopic or myopic eyes. This allows for providing an accurate eye examination even for subjects with hyperopia.

Furthermore, the step of determining an astigmatic axis angle determines the astigmatic axis of the subject, the step of determining hyperopia and myopia individually determines hyperopia and myopia in two orthogonal orientations selected in accordance with the astigmatic axis, and the step of determining a refractive power determines the refractive powers in two orthogonal orientations selected in accordance with the astigmatic axis. Thus, it is possible to determine lens power even on subjects with mixed astigmatism.

The step of determining an astigmatic axis angle preferably includes the steps of displaying a first astigmatic axis determination chart which includes four test symbols each having multiple straight lines arranged in parallel in four orientations at angles of about 45 degrees, about 90 degrees, about 135 degrees, and about 180 degrees, respectively, prompting the subject to select any test symbol viewed with greater contrast in the first astigmatic axis determination chart displayed, displaying a second astigmatic axis determination chart which includes four test symbols each having multiple straight lines arranged in parallel in four orientations approximately intermediate to the aforementioned four orientations, prompting the subject to select any test symbol viewed with greater contrast in the second astigmatic axis determination chart displayed, displaying a third astigmatic axis determination chart which includes the test symbol selected by the subject in the first astigmatic axis determination chart and the test symbol selected by the subject in the second astigmatic axis determination chart, prompting the subject to select any test symbol viewed with greater contrast in the third astigmatic axis determination chart displayed, and determining an astigmatic axis angle in accordance with the test symbol selected in the first astigmatic axis determination chart, the test symbol selected in the second astigmatic axis determination chart, and the test symbol selected in the third astigmatic axis determination chart.

The present invention allows the step of determining an astigmatic axis angle to display an astigmatic axis determination chart including a combination of the test symbols which have groups of multiple lines arranged in parallel at approximately 45 degree intervals in four limited orientations. The step then prompts the subject to select any test symbol viewed with greater contrast, thereby facilitating determination of astigmatic axes even by ordinary people, and thus, preventing erroneous determinations.

Furthermore, the step also displays the second astigmatic axis determination chart which has a combination of test symbols disposed in four orientations approximately intermediate to about 45 degrees, about 90 degrees, about 135 degrees, and about 180 degrees, and then prompts the subject to select any test symbol viewed with greater contrast. Additionally, the step also displays the third astigmatic axis determination chart which has a combination of the test symbols selected in the two astigmatic axis determination charts, and then prompts the subject to select any test symbol viewed with greater contrast. The astigmatic axis angle is thus determined in accordance with the test symbols selected in the three astigmatic axis determination charts. This allows for determining the astigmatic axis at an intermediate angle by calculation based on the angles of the test symbols selected in the three astigmatic axis determination charts. Thus, the astigmatic axis angle can be determined with substantially twice the resolution for the test symbols displayed in a total of eight orientations.

Furthermore, even when the subject has incorrectly selected some test symbols, the test symbols selected in the three astigmatic axis determination charts can be checked with each other to provide a correct determination. Thus, it is possible to determine the astigmatic axis angle of the subject with greater accuracy.

The step of determining hyperopia and myopia preferably includes the steps of displaying a first hyperopia and myopia determination chart having a red-based color background area and a blue-based color background area, in both of the areas black-based color straight lines are drawn in one of the two selected orthogonal orientations, prompting the subject to select the area which provides a clearer appearance of the straight lines to the subject in the first hyperopia and myopia determination chart displayed, displaying a second hyperopia and myopia determination chart having a red-based color background area and a blue-based color background area, in both of the areas black-based color straight lines are drawn in the other of the two selected orthogonal orientations, prompting the subject to select the area which provides a clearer appearance of the straight lines to the subject in the displayed second hyperopia and myopia determination chart, displaying a third hyperopia and myopia determination chart having a red-based color background area in which black-based color straight lines are drawn in the one of the two selected orthogonal orientations and a blue-based color background area in which black-based color straight lines are drawn in the other of the two selected orthogonal orientations, prompting the subject to select the area which provides a clearer appearance of the straight lines to the subject in the displayed third hyperopia and myopia determination chart, displaying a fourth hyperopia and myopia determination chart having a red-based color background area in which black-based color straight lines are drawn in the other of the two selected orthogonal orientations and a blue-based color background area in which black-based color straight lines are drawn in the one of the two selected orthogonal orientations, prompting the subject to select the area which provides a clearer appearance of the straight lines to the subject in the displayed fourth hyperopia and myopia determination chart; and determining hyperopia and myopia at the astigmatic axis angle determined and at an angle orthogonal thereto in accordance with a result selected in the first hyperopia and myopia determination chart, a result selected in the second hyperopia and myopia determination chart, a result selected in the third hyperopia and myopia determination chart, and a result selected in the fourth hyperopia and myopia determination chart.

The step of determining hyperopia and myopia using a test symbol which has a red-based color background area and a blue-based color background area and black-based color straight lines drawn in both of the areas in either one of the two orthogonal orientations selected in accordance with the astigmatic axis angle determined through the step of determining an astigmatic axis angle. The step of determining hyperopia and myopia displays the first hyperopia and myopia determination chart having straight lines drawn in both of the areas in one of the two orientations, the second hyperopia and myopia determination chart having straight lines in both of the areas in the other of the two orthogonal orientations, the third hyperopia and myopia determination chart having straight lines which are drawn in the one of the two orientations in one area and which are drawn in the other of the two orientations in the other area, and the fourth hyperopia and myopia determination chart having straight lines which are drawn in the other of the two orientations in one area and which are drawn in the one of the two orientations in the other area. The step of determining hyperopia and myopia prompts the subject to select the area which provides a clearer appearance of the straight lines to the subject in each of the hyperopia and myopia determination charts, thereby determining the hyperopia or myopia at the astigmatic axis angle of the subject and at an angle orthogonal thereto.

This is achieved by a phenomenon that the red-based color area provides a clearer appearance to a myopic eye whereas the blue-based color area provides a clearer appearance to a hyperopic eye. This phenomenon results from the fact that when the red-based color area and the blue-based color area are viewed by the human eye at the same time, chromatic aberration causes the red-based color to be focused rearward and the blue-based color to be focused frontward. Accordingly, the subject is only required to determine which area provides a clearer appearance.

Furthermore, this hyperopia and myopia determination chart also indicates directive test symbols having straight lines which are oriented in two orthogonal orientations selected in accordance with the astigmatic axis angle determined through the step of determining an astigmatic axis angle and which are drawn in the two color areas exhibiting chromatic aberration. Thus, it is possible to detect the dependency of hyperopia and myopia on angle. This allows for determining hyperopia and myopia independently at the astigmatic axis angle of the subject and at an angle orthogonal thereto, respectively. Thus, this is also applicable to subjects with mixed astigmatism.

Furthermore, hyperopia and myopia are to be determined using the two additional hyperopia and myopia determination charts, in each of which straight lines are drawn in each of the areas in two different orientations in addition to the two hyperopia and myopia determination charts, in each of which straight lines are drawn in both of the areas in one of two orientations. Accordingly, even when the subject makes some erroneous determinations, it is possible to check the results selected in the four charts with each other, thereby enabling the correct determination. This allows for determining hyperopia and myopia at the astigmatic axis angle of the subject and at an angle orthogonal thereto with greater accuracy.

When, the subject has selected either the "red-based color area" or "Viewed equally" but not the "blue-based color area" in both of the first hyperopia and myopia determination chart and the second hyperopia and myopia determination chart, the subject is considered to have no hyperopic factor, and thus, the determinations using the third hyperopia and myopia determination chart and the fourth hyperopia and myopia determination chart may be omitted. This provides for more efficient determination of hyperopia and myopia.

The step of determining a refractive power preferably includes the steps of sequentially displaying a plurality of refractive power determination charts which have a combination of test symbols having a number of straight lines drawn in parallel in the two selected orthogonal orientations in which the step difference in size is two or more, prompting the subject to select the smallest viewable test symbol in each of the refractive power determination charts displayed, and determining refractive powers at the determined astigmatic axis angle and at an angle orthogonal thereto in accordance with the test symbols selected in each of the refractive power determination charts.

The present invention allows the step of determining a refractive power to sequentially display a plurality of refractive power determination charts which have a combination of test symbols in which the step difference in size is two or more corresponding to refractive powers. Here, the test symbols include a specific number of straight lines drawn in parallel in the two orthogonal orientations selected in accordance with the astigmatic axis angle determined through the step of determining an astigmatic axis angle. The step of determining a refractive power then prompts the subject to select the smallest test symbol in which the number of straight lines can be accurately recognized in each refractive power determination chart. Accordingly, as compared to the conventional Landoldt ring having a partial break rotated for determination, it is possible to provide test symbols in a larger number of step size. This makes it possible to increase resolution in determination of refractive powers, thereby accurately determining the refractive powers at the astigmatic axis angle of the subject and the angle orthogonal thereto.

Since the refractive power determination charts which have a combination of test symbols in which the step difference in size is two or more are used, the subject does not have to make a subtle determination to select the smallest viewable test symbol among test symbols having a small step difference in size, thereby facilitating the selection of the smallest viewable test symbol.

Furthermore, since determinations in a plurality of refractive power determination charts are combined to determine the smallest viewable test symbol, even when some erroneous determinations are made by the subject due to pseudo-resolution, it is possible to accurately determine the refractive powers by checking the determinations with each other. This allows for determining the refractive powers at the astigmatic axis angle of the subject and at an angle orthogonal thereto with greater accuracy.

In particular, it is preferable to use three refractive power determination charts in which the step difference in size of the test symbols is three. This allows the subject to easily select the smallest viewable test symbol and determine the refractive powers with greater accuracy through the three determinations.

The step of determining a refractive power preferably includes a far refractive power determination step of prompting the subject to view test symbols at a far distance from display means and select the smallest viewable test symbol, a near refractive power determination step of prompting the subject to view test symbols at a close distance to the display means and select the smallest viewable test symbol, and a step of determining the refractive powers at the determined astigmatic axis angle and at an angle orthogonal thereto in accordance with the test symbol selected through the far refractive power determination step and the test symbol selected through the near refractive power determination step.

Typically, a computer screen is viewed at approximately a subject's reach (about 60 cm to about 70 cm). However, some people with hyperopia or presbyopia are within the range of accommodation at this distance because it is farther than the near point distance, thus not being able to determine their refractive power.

The present invention enables the step of determining a refractive power to include the far refractive power determination step of prompting test symbols to be viewed at a far distance from display means for determination of refractive powers, and the near refractive power determination step of determining refractive powers at a near distance to the display means. The refractive power determination step has a step to determine the refractive powers at the astigmatic axis angle and at an angle orthogonal thereto in accordance with the test symbol selected through the far refractive power determination step and the test symbol selected through the near refractive power determination step.

Accordingly, the refractive power of a subject having hyperopia or presbyopia, who is within the range of accommodation through the far refractive power determination step, can be determined.

Furthermore, when the step of determining hyperopia and myopia could not determine hyperopia and myopia, it is possible to use the test symbol selected in the far refractive power determination and the test symbol selected in the near refractive power determination to determine hyperopia and myopia and calculate the refractive power at the astigmatic axis angle of the subject and at an angle orthogonal thereto. For example, a difference in size between the test symbol selected in the far refractive power determination and the near refractive power determination may be obtained. If the difference is positive and equal to or greater than a specific value (i.e., a near test symbol provides a clearer appearance), the subject may be determined to have myopia. Otherwise, if the difference is negative and equal to or less than a specific value (i.e., a far test symbol provides a clearer appearance), the subject may be determined to have hyperopia. Alternatively, a difference in size between the test symbols selected in the far refractive power determinations in two orthogonal orientations and a difference in size between the test symbols selected in the near refractive power determinations in two orthogonal orientations may be obtained. If the differences are equal to each other in sign and the former is greater than the latter, their average may be determined as an astigmatic refractive power.

On the other hand, even when hyperopia and myopia have been determined in the step of determining hyperopia and myopia, the test symbol selected in the far refractive power determination and the test symbol selected in the near refractive power determination may be checked with each other, thereby correcting any errors made by the subject. Moreover, in the determination of refractive powers, both the test symbol selected in the far refractive power determination and the test symbol selected in the near refractive power determination may be used to determine the refractive power by calculation. This enables more accurate determinations of the hyperopia and myopia and more accurate determinations of the refractive power determination at the astigmatic axis angle of the subject and at an angle orthogonal thereto.

Typically, a computer screen is viewed at approximately a subject's reach, and most people with hyperopia or presbyopia have a near point distance of at least 30 cm. Accordingly, the far refractive power determination may be made, e.g., at a subject's reach (about 60 cm to about 70 cm) to the display means, whereas the near refractive power determination may be made, e.g., at a distance of an A4-size piece of paper (about 30 cm) disposed longitudinally between the eye of the subject and the display means.

The step of determining a refractive power preferably includes the steps of displaying a refractive power determination chart having test symbols varied in size in a stepwise manner, each of the test symbols having a line group area with red-based color straight lines and blue-based color straight lines of a uniform width drawn alternately in the two selected orthogonal orientations, and a reference color area of the same color as either one of the straight lines in the line group area, prompting the subject to select the smallest test symbol in the refractive power determination chart displayed in which any straight lines in the line group area provide an appearance of the same color as that of the reference color area, and determining the refractive powers at the astigmatic axis angle determined and at an angle orthogonal thereto in accordance with the test symbol selected in the refractive power determination chart.

The present invention uses a refractive power determination chart which includes test symbols varied in size in a stepwise manner according to refractive powers to determine refractive powers. The test symbols include the line group area with red-based color straight lines and blue-based color straight lines drawn alternately and the reference color area of the same color as either one of the straight lines in the line group area.

With this configuration, refractive powers are determined using the following fact. That is, when the subject views the test symbols having straight lines drawn in two colors, a test symbols having the straight lines spaced within the resolution of the eye provide an appearance of two properly separated colors. However, test symbols having the straight lines spaced beyond the resolution of the eye provide an appearance of the two colors being mixed up.

This allows for the subject to intuitively determine the smallest viewable test symbol while alleviating the problem that pseudo-resolution causes the subject to incorrectly determine the number of straight lines.

The colors to be used are not necessarily limited to the red-based color and blue-based color. Any combination of colors may also be used as long as the colors being mixed up can be properly recognized by the subject.

Here, the test symbols varied in size in a stepwise manner corresponding to refractive powers were used for the subject to select the smallest viewable test symbol. However, it is also acceptable to use a test symbol having two colors placed radially alternately, and thereby determine refractive powers in accordance with the distance from the center to the position nearest to the center at which the two colors can be separately recognized. In this case, since the refractive powers corresponding to orientations can also be determined, the astigmatic axis angle determination and refractive power determination may be performed simultaneously. Furthermore, for example, the combination of colors to be mixed in longer wavelengths and that in shorter wavelengths may be combined together such that the astigmatic axis determination, the hyperopia and myopia determination, and the refractive power determination may be performed simultaneously. This makes it possible to perform a lens power determination in a very efficient manner.

The step of determining a refractive power preferably includes the step of sequentially displaying a plurality of refractive power determination charts having a combination of test symbols having a line group area with red-based color straight lines and blue-based color straight lines of a uniform width drawn alternately in the two selected orthogonal orientations in which the step difference in size is two or more, and a reference color area of the same color as either one of the straight lines in the line group area, prompting the subject to select the smallest test symbol in each of the refractive power determination charts displayed in which any straight lines in the line group area provide an appearance of the same color as that of the reference color area, and determining the refractive powers at the determined astigmatic axis angle and at an angle orthogonal thereto in accordance with the test symbol selected in each of the refractive power determination charts.

The present invention sequentially displays a plurality of refractive power determination charts which include test symbols in which the step difference in size of the test symbols is two or more corresponding to refractive powers to determine refractive powers. The refractive power determination charts include the line group area with red-based color straight lines and blue-based color straight lines drawn alternately and the reference color area of the same color as either one of the straight lines in the line group area.

In this manner, by using a mixture of two colors, viewability is determined. This allows the subject to intuitively determine the smallest viewable test symbol while alleviating the problem of pseudo-resolution causing the subject to incorrectly determine the number of straight lines.

Since the refractive power determination charts which include a combination of test symbols in which the step difference in size is two or more are used, the subject is prevented from making a subtle determination to select the smallest viewable test symbol among test symbols having a small step difference in size, thereby facilitating the selection of the smallest viewable test symbol.

Furthermore, since determinations in a plurality of refractive power determination charts are combined to determine the smallest viewable test symbol, even in the presence of some erroneous determinations made by the subject due to pseudo-resolution, it is possible correctly determine refractive powers by checking the determinations with each other. This allows for determining the refractive powers at the astigmatic axis angle of the subject and at an angle orthogonal thereto with greater accuracy.

In particular, it is preferable to use three refractive power determination charts in which the step difference in size of the test symbols is three. This allows the subject to easily select the smallest viewable test symbol and determine the refractive powers with accuracy through the three determinations.

The lens power determination method preferably includes the steps of displaying a rough determination chart in which test symbols having no directivity are varied in size in a stepwise manner, prompting the subject to select the smallest viewable test symbol in the rough determination chart displayed, and determining a subject's rough view, wherein the step of determining an astigmatic axis angle and/or the step of determining hyperopia and myopia and/or the step of determining a refractive power have a step of varying the condition of the test symbol to be displayed in accordance with the determined rough view.

The present invention provides the rough determination step to determine a subject's rough view using the rough determination chart, while the condition of the test symbols to be displayed is varied in accordance with the rough view in the astigmatic axis angle determination step, in the hyperopia and myopia determination step, or in the refractive power determination step. This reduces the time required for the eye examination and facilitates the determination by the subject, thereby making it possible to perform the lens power determination with greater accuracy.

The rough determination chart uses test symbols having no directivity. Thus, even when a subject has astigmatism, it is possible to determine the rough view independent of the astigmatic axis angle.

These and other objects, features, and advantages of the present invention will be readily apparent from the following detailed description of the embodiments of the invention, when taken in connection with the accompanying drawings.

DETAILED DESCRIPTION OF PREFERRED EMBODIMENTS

Figure 1:
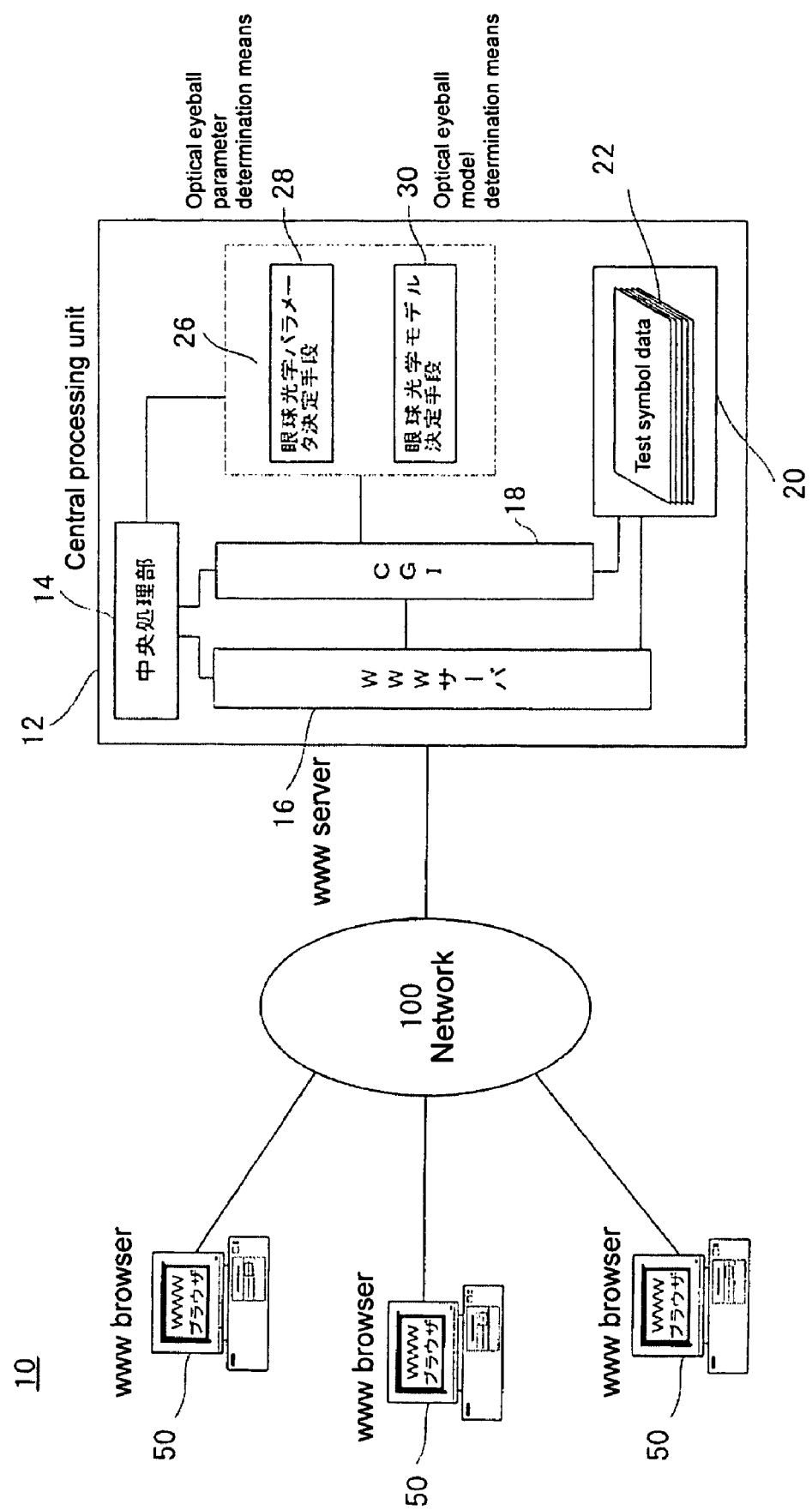
FIG. 1 is a system configuration of an optometric apparatus according to a preferred embodiment of the present invention.

FIG. 1 is a system configuration of an optometric apparatus according to a preferred embodiment of the present invention. As shown, an optometric apparatus 10 includes an eye examination server 12, a subject terminal 50, and a network 100.

The eye examination server 12 provides data such as test symbol data to the subject terminal 50, and determines astigmatic axes, hyperopia or myopia, and refractive powers of subjects based on results entered on the subject terminal 50, thereby performing subjective eye examinations. As the hardware for the eye examination server 12, computers such as personal computers, workstations, or servers are provided. The eye examination server 12 can have various applications installed therein to thereby provide various services. The eye examination server 12 also includes a modem or network interface card (not shown) for two-way communications with the subject terminal 50 via the network 100.

The eye examination server 12 includes a central processing unit 14. The central processing unit 14 controls and manages the operation of each of the means discussed later.

The central processing unit 14 is connected with a WWW server 16 for providing test symbol data. The WWW server 16 provides a function to conduct two-way data communications with the subject terminal 50 via the network 100. The WWW server 16 transmits HTML data, image data, and various types of programs to the subject terminal 50 in accordance with the contents entered or manipulated using input means, such as a mouse or keyboard (not shown) at the subject terminal 50. The WWW server 16 also receives data which has been entered at and transmitted from the subject terminal 50.

The WWW server 16 is connected with a CGI 18. The CGI 18 provides a function to dynamically create HTML data corresponding to the contents of the data transmitted from the subject terminal 50, and then to deliver the resulting HTML data to the WWW server 16.

The CGI 18 also extracts data regarding the state of viewing of test symbols by a subject from the data delivered from the WWW server 16. Then, the CGI 18 delivers the data thus extracted and obtained to optical eyeball parameter determination means 28.

The WWW server 16 reads various data from a storage area 20 in which test symbol data 22 is stored. The test symbol data 22 is data indicating the images of test symbols for use with eye examinations. The test symbol data 22 is stored as image data of various types such as JPEG, PNG, GIF, animation GIF, or Flash (a trademark by MACROMEDIA). The test symbol data 22 is transmitted to the subject terminal 50 as part of HTML data to be displayed on a display device of the subject terminal 50. Various types of the test symbol data 22 are stored which corresponds to the contents of determinations. Now, the test symbol data 22 which is used for determination will be described.

The test symbol data 22 includes test symbols 22a for determining rough views, test symbols 22b for determining astigmatic axes, test symbols 22c for determining hyperopia and myopia, and test symbols 22d for determining refractive powers.

Figure 2:
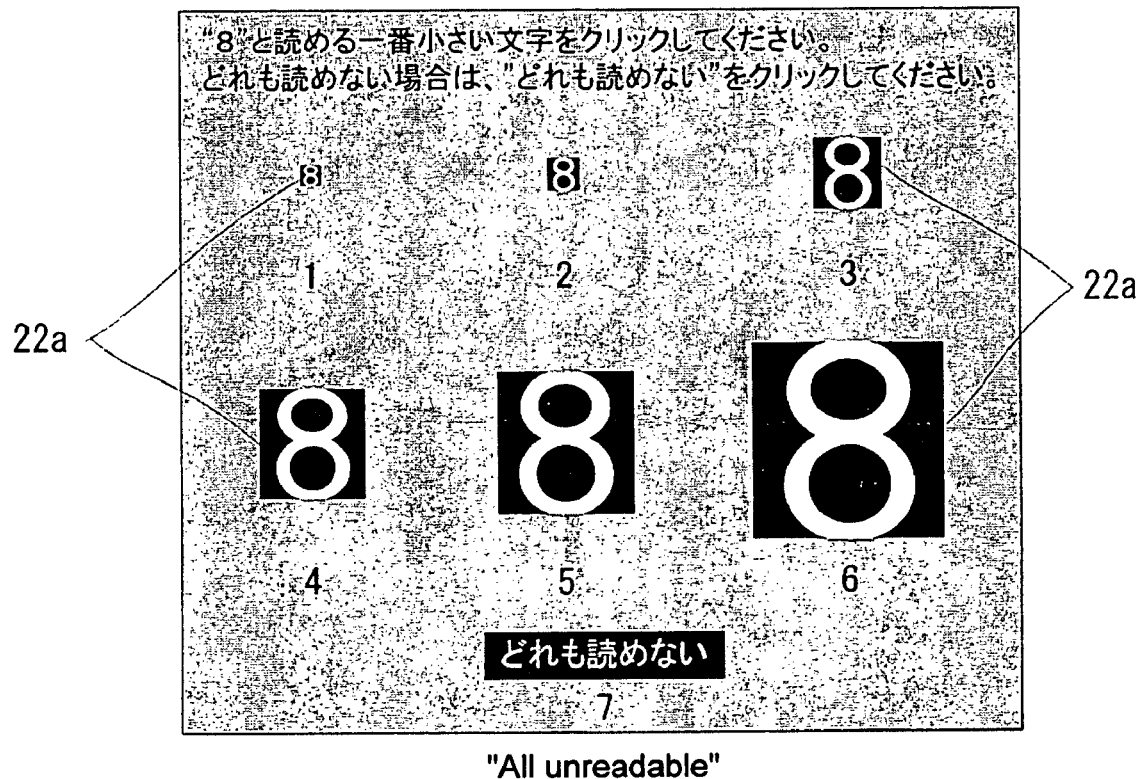
FIG. 2 is a view showing an example of a rough view determination chart.

The test symbols 22a for determining rough views are symbols which have no directivity but have a specific thickness. Used here as the test symbols 22a are a white on black numeric character "8," which has two endless annular rings disposed as two circles being in contact with each other and rendered with a white bold line having a desired width on a black background. The test symbols 22a which have sizes that are varied in a stepwise manner corresponding to rough view rankings are arranged in the rough determination chart (FIG. 2).

The rough determination chart displayed on the screen of the subject terminal is viewed from a specific distance to select the smallest viewable test symbol, thereby making a rough view determination.

As mentioned above, the symbols used in the rough view determination chart have no directivity. This is because symbols with many straight lines oriented in the same direction may cause a person having an astigmatic composition in a particular direction to make an erroneous determination. Accordingly, when the subjects are restricted only to those without astigmatism, such characters or symbols as having many straight lines may be used as test symbols. As used herein, these test symbols are numeric characters "8" rendered with white bold lines. However, black lines rendered on a bright background may also be used, or alternatively donut-shaped or double or triple circles, which have no directivity, may also be used.

The test symbols 22b for determining astigmatic axes have multiple straight black lines of a specific width which are spaced in parallel at equal distances on a green background in this preferred embodiment. The test symbols 22b are used in the first, second, and third astigmatic axis determination charts. The first astigmatic axis determination chart (FIG. 3) includes a combination of four test symbols having straight lines oriented at angles of about 45 degrees, about 90 degrees, about 135 degrees, and about 180 degrees, respectively. The second astigmatic axis determination chart (FIG. 4) includes a combination of four test symbols having straight lines oriented at angles of about 23 degrees, about 68 degrees, about 113 degrees, and about 158 degrees, respectively. The third astigmatic axis determination chart (FIGS. 5, 6, and 7) includes a combination of the test symbols selected in accordance with a determination in the first astigmatic axis determination chart and a determination in the second astigmatic axis determination chart.

The determination of an astigmatic axis angle is performed by, first, displaying the first astigmatic axis determination chart on the subject terminal and prompting the subject to select any test symbol viewed with greater contrast, then displaying the second astigmatic axis determination chart and prompting the subject to select any test symbol viewed with greater contrast, and in case astigmatic axis angle cannot be determined using these two charts, displaying the third astigmatic axis determination chart which includes a combination of the test symbols selected in the two charts and prompting the subject to select any test symbol viewed with greater contrast, thereby determining the astigmatic axis angle. In this manner, the determination using the test symbols having straight lines oriented at angles of about 45 degrees, about 90 degrees, about 135 degrees, and about 180 degrees and the determination using the test symbols having straight lines oriented at angles of about 23 degrees, about 68 degrees, about 113 degrees, and about 158 degrees, which are in between the aforementioned angles are combined, thereby making it possible to determine intermediate angles therebetween in appearance. Thus, it is possible to determine the astigmatic axis angle substantially with twice as much resolution as the smallest angle difference between the test symbols used.

The test symbols 22b have straight black lines arranged in a green background to prevent the pupil of the subject from being miosis in this preferred embodiment. However, test symbols of any color combinations may also be used as long as the test symbols have a sufficient contrast to distinguish between the straight lines and the background and prevent the pupil of the subject from being miosis.

The test symbols 22c for determining hyperopia and myopia have a rectangular frame divided into equal right and left areas, the left area having a red background and the right area having a blue background in this preferred embodiment. In each area, close to the boundary of both areas, straight black lines of a specific width are spaced in parallel at equal distances. The test symbols 22c are used as the first, second, third, and fourth hyperopia and myopia determination charts. The first hyperopia and myopia determination chart (FIG. 8(a)) includes the areas with straight lines oriented corresponding to an astigmatic axis angle. The second hyperopia and myopia determination chart (FIG. 8(b)) includes the areas with straight lines oriented corresponding to an angle orthogonal to the astigmatic axis angle. The third hyperopia and myopia determination chart (FIG. 8(c)) includes the red area with straight lines oriented corresponding to an astigmatic axis angle and the blue area with straight lines oriented corresponding to an angle orthogonal to the astigmatic axis angle. Finally, the fourth hyperopia and myopia determination chart (FIG. 8(d)) includes the red area with straight lines oriented corresponding to an angle orthogonal to an astigmatic axis angle and the blue area with straight lines oriented corresponding to the astigmatic axis angle.

Hyperopia or myopia is determined by displaying the charts on the subject terminal and prompting the subject to select the area, either the red or blue area, which provides a clearer appearance of the straight lines to the subject. This is realized by utilizing the phenomenon that either one of the test symbols provides a clearer appearance which is different between those with hyperopia and those with myopia. This phenomenon results from the fact that when red beam and blue beam of light are incident upon the eyeball, chromatic aberration causes the blue beam to be focused frontward and the red beam rearward. Accordingly, the background of the test symbols 22c is not limited to the colors of blue and red, but may also be any combination of colors as long as the chromatic aberration causes the aforementioned phenomenon. As for the straight lines, any colors may also be used as long as the colors have good contrast against the background of each area and enable selection of a clearer appearance of either one of the areas.

When either "Red area" or "Viewed equally" is selected through the determinations in both the first hyperopia and myopia determination chart and the second hyperopia and myopia determination chart, the subject is considered to indicate emmetropia or myopia. Thus, in this case, the determinations in the third hyperopia and myopia determination chart and the fourth hyperopia and myopia determination chart are omitted. The determinations in the third hyperopia and myopia determination chart and the fourth hyperopia and myopia determination chart are performed only when the "blue area" is selected through the determination in either the first hyperopia and myopia determination chart or the second hyperopia and myopia determination chart.

In this preferred embodiment, each area includes a rectangular frame for convenience. However, the rectangular frame is not necessarily used, and instead a circular frame or other suitable frame may be used. In addition, the test symbols shown in FIG. 8 have straight lines drawn at angles of 90 degrees and 180 degrees. However, the test symbols used in practice have straight lines drawn in two orthogonal orientations selected in accordance with the astigmatic axis angle of the subject. Accordingly, other than the hyperopia and myopia determination charts shown in FIG. 8, charts which include combinations of test symbols having straight lines drawn at angles of about 45 degrees and about 135 degrees, at angles of about 23 degrees and about 113 degrees, and at angles of about 68 degrees and about 158 degrees, respectively, will also be used.

Astigmatic axis angles may be provided in the central orientations in increments of about 23 degrees by calculation. However, it is difficult to draw straight lines on ordinary display devices in the central orientations in increments of about 23 degrees, and it is possible to perform a determination even with the orientation of test symbols does not precisely coincide with the astigmatic axis angle. Accordingly, the closest one of the orientations in increments of about 23 degrees is selected to determine hyperopia or myopia. Therefore, when high resolution display means are used as the subject terminal, a determination may be performed on hyperopia and myopia using test symbols drawn in small increments of angles corresponding to the determined astigmatic axis angle.

Figure 9:
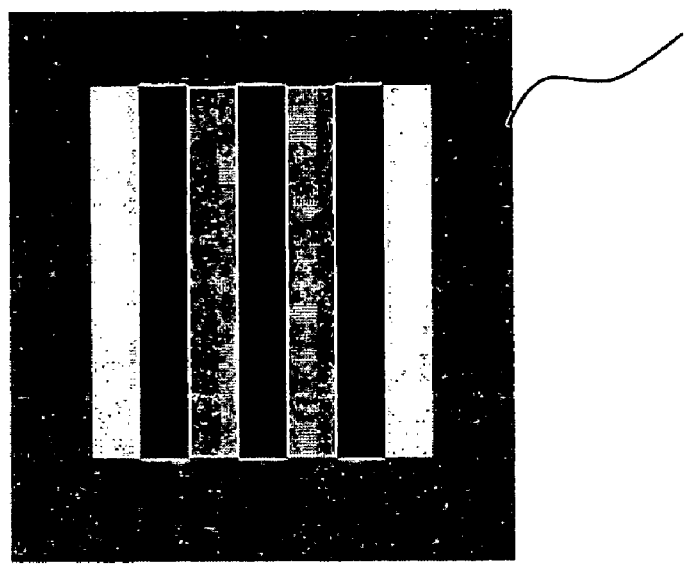
FIG. 9 is a view showing an example of a refractive power determination test symbol.

The test symbol 22d (FIG. 9) for determining refractive powers includes three straight black lines of a desired width spaced at equal distances and provided on a green background, with yellow side zones of the same width as that between the lines provided on both outside ends of the three straight lines in the direction of their width in this preferred embodiment. A number of test symbols 22d are provided and include symbols having sizes that are varied in a stepwise manner corresponding to refractive powers. Combinations of test symbols in which the step difference in size is three are used as the first refractive power determination chart (FIG. 10), the second refractive power determination chart (FIG. 11), and the third refractive power determination chart (FIG. 12) in this preferred embodiment.

The determination of refractive powers is performed in the following manner: each of the refractive power determination charts is sequentially displayed on the subject terminal, prompting the subject to select the smallest test symbol that provides an appearance of three straight black lines in each chart. The test symbols selected in each chart are checked with each other to determine the smallest viewable test symbol, thereby determining the refractive power.

The three charts each including a combination of test symbols of sizes different from each other by three steps are used for the determination of refractive powers in this preferred embodiment. This allows the subject to easily select the smallest viewable test symbol and the selections are to be checked with each other, thereby providing a result of determination with high reliability. Accordingly, refractive powers may also be determined using charts each including test symbols in which the step difference in size is one as long as those charts permit the subject to select the smallest viewable test symbol. In this case, refractive powers may be divided into classes, such that a plurality of charts each having a combination of test symbols are used to determine the refractive power for each of the classes. On the other hand, the step difference in size may be further increased to further facilitate the selection of test symbols by the subject. However, this may increase the number of charts, thereby extending time to perform the determination.

The side zones are provided in the test symbol, because without the side zones, a faint black line would appear outside the three lines in the presence of pseudo-resolution, thereby making it difficult to determine whether these faint lines should be counted as a number of the lines. However, the presence of the bright side zones will provide good contrast against the lines resulting from the pseudo-resolution, thereby facilitating the determination. Additionally, without the side zones, the appearance of test symbols having a size that is smaller than the smallest viewable test symbol would be gradually defocused, thereby making it difficult to determine the limit of viewing. However, the presence of the side zones will cause the black lines, areas between the lines, and side zones to be jumbled, and thus, defocused in a smaller test symbol, thereby facilitating the determination of the limit of viewing. Accordingly, the side zones are preferably different in color from the areas between the lines and higher in brightness than the areas between the lines. Furthermore, the width of side zones is about 0.5 to about 2 times the width of the black lines to provide the aforementioned effects.

The areas between the lines and side zones in a test symbol are preferably a color other than red or blue because the determination with these colors may be affected by chromatic aberration. The color of the areas between the lines is preferably either one of monochrome, green, or yellow, while the color of side zones is preferably monochrome or yellow. Thus, the areas between the lines are of slightly brighter green than the background, while the side zones are yellow and brighter than the areas between the lines and different therefrom in color in this preferred embodiment.

Figure 10:
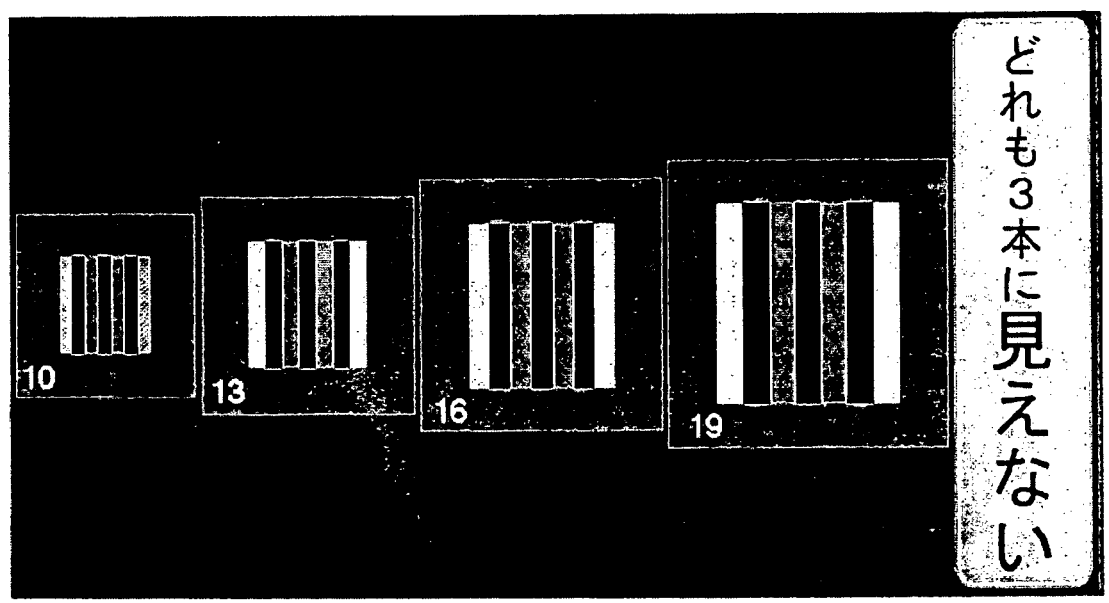
FIG. 10 is a view showing an example of a first refractive power determination chart.
Figure 11:
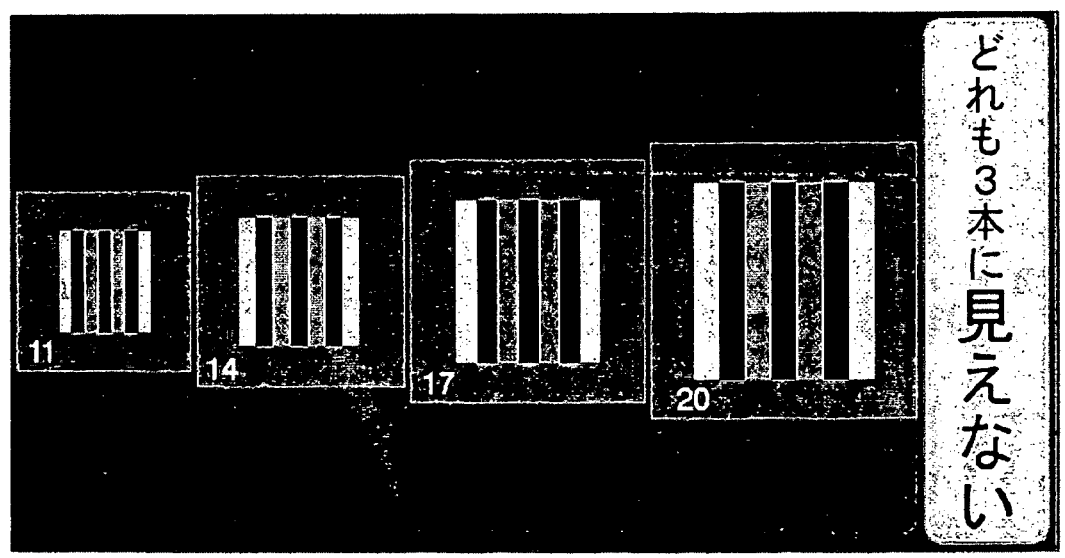
FIG. 11 is a view showing an example of a second refractive power determination chart.
Figure 12:
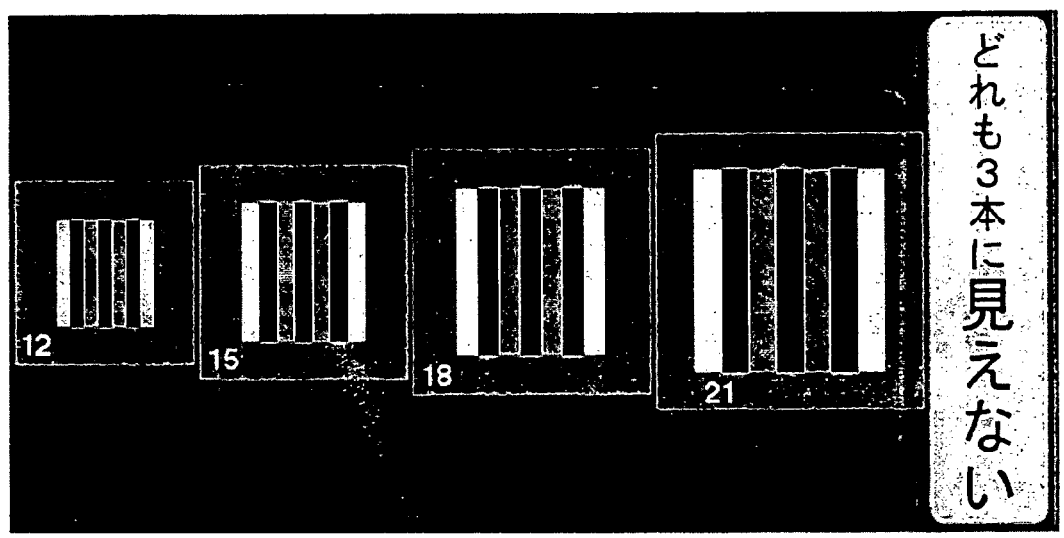
FIG. 12 is a view showing an example of a third refractive power determination chart.

On the other hand, the test symbols, shown in the charts of FIGS. 10 to 12, have straight lines oriented at an angle of 180 degrees. However, the test symbols used in practice have straight lines drawn in two orthogonal orientations selected in accordance with the astigmatic axis angle of the subject. Accordingly, other than the hyperopia and myopia determination charts shown in FIG. 8, charts will be used which include test symbols having straight lines drawn at angles of about 90 degrees, about 45 degrees, or about 135 degrees.

This refractive power determination chart uses no test symbols having straight lines drawn in the orientations of about 23 degrees, about 68 degrees, about 113 degrees, or about 168 degrees because of the following reasons. That is, the refractive powers at an astigmatic axis angle and at an angle orthogonal thereto have small errors even with the orientation of the test symbols not exactly coinciding with the astigmatic axis angle. In addition, since straight lines oriented at angles in increments of about 23 degrees appear jagged on a computer screen having an ordinary resolution, it is difficult to determine whether the straight lines are properly viewed, thereby possibly causing an erroneous determination. For these reasons, one of the angles formed in increments of about 45 degrees which is closest to the astigmatic axis angle determined in the astigmatic axis determination chart and an angle orthogonal thereto is selected to determine refractive powers. Accordingly, with high-resolution display means used as the subject terminal, it may also be acceptable to use test symbols formed at angles in smaller increments corresponding to the astigmatic axis angle determined in order to determine refractive powers. On the other hand, the astigmatic axis angle of the subject may be in between the angles of the test symbols 22d oriented at angles in increments of 45 degrees. In this case, refractive powers may be determined using the test symbols oriented at both the angles adjacent to the astigmatic axis angle, and the resulting refractive powers may be weighted to determine the refractive power at the astigmatic axis angle.

The determination of refractive powers includes a "far refractive power determination" which is performed with the screen placed at the reach of the subject (hereinafter referred to as the "subject's reach") and a "near refractive power determination" which is performed at a distance of an A4-size piece of paper disposed longitudinally between the screen and the eye (hereinafter referred to as the "A4-sized-paper distance." Usually, only the "far refractive power determination" is performed. However, for the subjects at ages of 40 or older who have hyperopia and a determination being suspended for hyperopia and myopia, the "near refractive power determination" is also performed and the two results are checked with each other to determine refractive powers.

Figure 13:
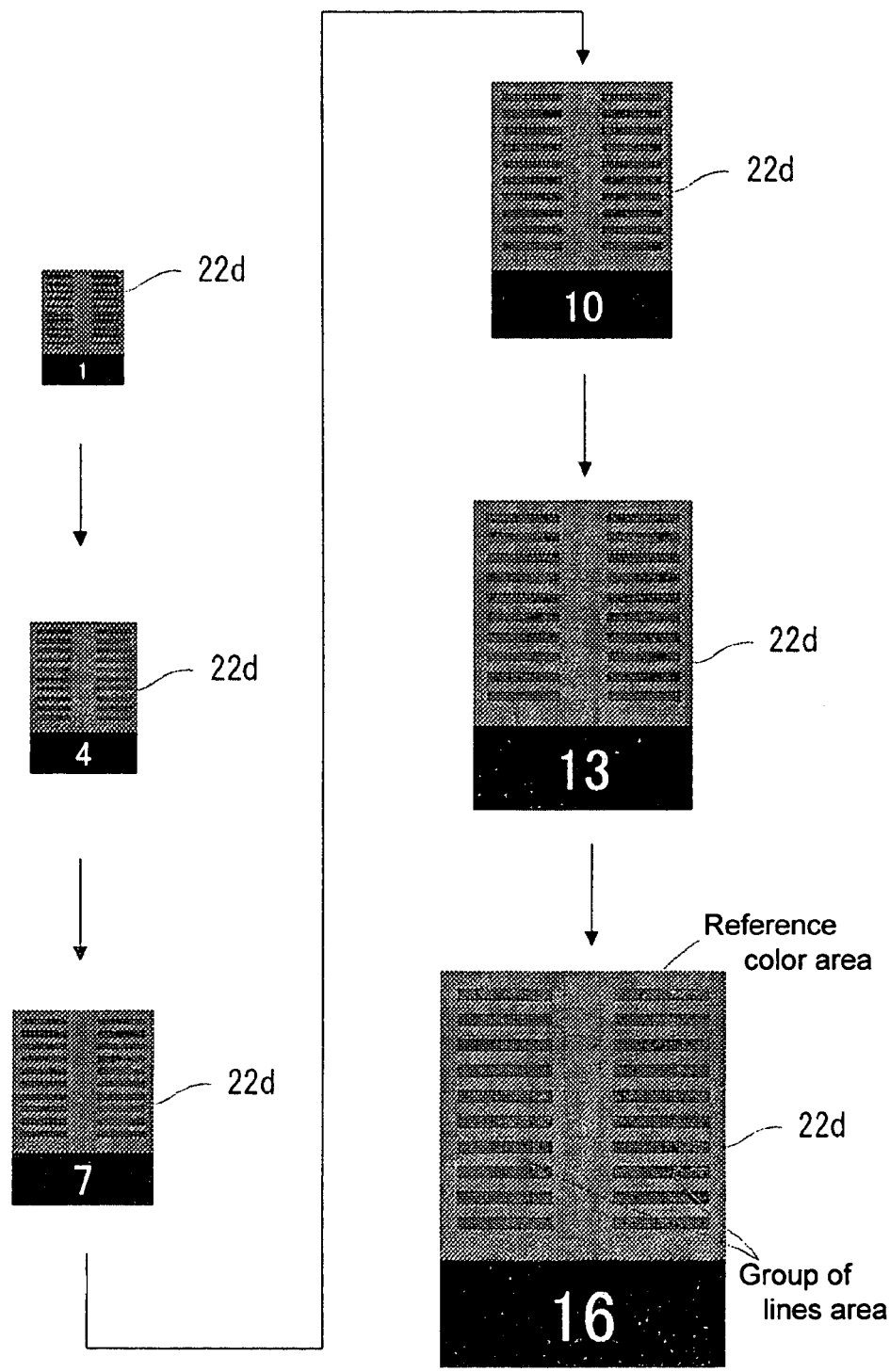
FIG. 13 is a view showing another example of a refractive power determination chart.

As the test symbols 22d for determining refractive powers, a test symbol having a rectangular frame may be used which includes a line group area having straight red lines and blue lines of a specific width spaced in parallel at equal intervals and which also includes a reference color area having the same color as that of the red lines (FIG. 13). This is to determine refractive powers in accordance with the following fact. That is, when viewed by the subject, the line group area of a test symbol having the red lines and the blue lines spaced at larger intervals than the resolution of the eye corresponding to its visual acuity can appear separately in the two colors. However, such a test symbol having the lines spaced at intervals less than the resolution of the eye corresponding to its visual acuity is mixed up in color to provide a pink appearance.

As shown in FIG. 13, the determination of refractive powers using these test symbols can be performed by displaying the test symbols varied in size in a stepwise manner corresponding to refractive powers in the increasing order of size on the subject terminal, and prompting the subject to select the test symbol whose red lines in the line group area have first changed from a pink to the same red appearance as that of the reference color area.

Alternatively, a chart including a combination of test symbols varied in size in a stepwise manner corresponding to refractive powers may be displayed on the subject terminal to prompt the subject to select the smallest test symbol that provides the appearance of the lines of the line group area in the same color as that of the reference color area.

Alternatively, three charts each including a combination of test symbols varied in size by three steps, just like the aforementioned test symbols, may be displayed on the subject terminal to prompt the subject to select the smallest test symbol in each chart that provides the appearance of the lines of the line group area in the same color as that of the reference color area. Then, the test symbols selected from each of the charts may be checked with each other to determine the smallest viewable test symbol, thereby determining the refractive power.

Test symbols having their entire frames inclined such that the line group area is oriented at angles of about 45 degrees, about 90 degrees, about 135 degrees, and about 180 degrees are also available for determining refractive powers in two orientations selected in accordance with the astigmatic axis angle of the subject.

Figure 14:
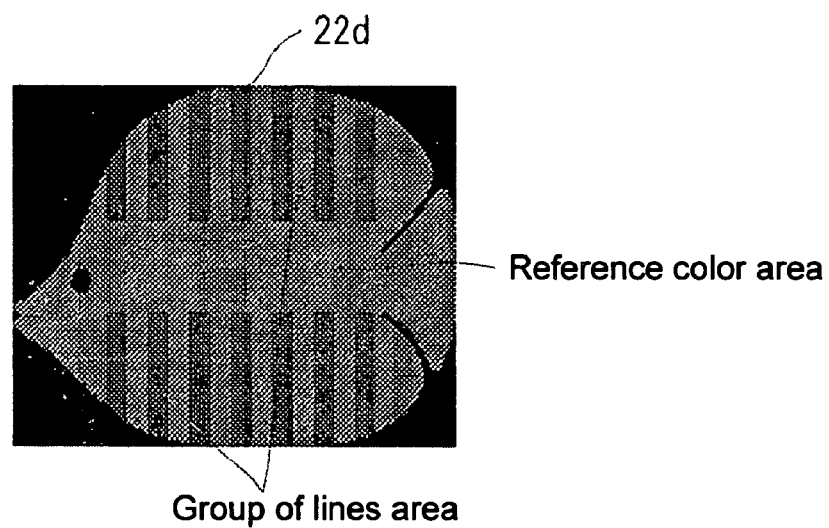
FIG. 14 is a view showing another example of a refractive power determination test symbol.

In the aforementioned preferred embodiment, the test symbols are to be displayed within a rectangular frame. However, the outline is not necessarily rectangular, and may also be round. For example, as shown in FIG. 14, a representation of a fish having a skeletal body may also be acceptable. This allows for calling the line group area as the "fish ribs," which may be more understandable to the subject, or for calling the reference color area as the "fish center bone," thereby providing an eye examination in a more friendly environment. In the foregoing, the color of the reference color area is the same as that of the red lines. The color of the reference color area may also be the same as that of the blue lines. The reference color area was disposed in contact with the line group area. However, the present invention is not limited thereto. The reference color area may be provided at any location as long as the position allows for instantaneously determining that the reference color area is the same in color as one of the lines in the line group area when viewed by the subject.

The size and brightness of test symbols displayed on the subject terminal may vary depending on the type of display devices (CRT or liquid crystal display), the size (such as 14" or 17"), and the screen resolution (such as 800×600 or 1027× 768). Thus, a plurality of pieces of test symbol data are stored which include various sizes and levels of brightness in order to display test symbols of the predetermined size and brightness on any display devices. It is also acceptable that each test symbol data is created through image processing in accordance with the condition of the display device.

The CGI 18 is connected with an eye examination function part 26.

The eye examination function part 26 includes the optical eyeball parameter determination means 28 and optical eyeball model determination means 30. The eye examination function part 26 performs an eye examination on the subject and determines an approximate refractive power to formulate an optical eyeball model, thereby selecting glasses or contact lenses suitable for the subject.

Using the aforementioned test symbols, the optical eyeball parameter determination means 28 provides functions to perform the rough determination processing for determining a subject's rough view, the astigmatic axis determination processing for determining astigmatic axis angles, the hyperopia and myopia determination processing for determining hyperopia and myopia at an astigmatic axis angle and at an angle orthogonal thereto, and the refractive power determination processing for determining the refractive powers at an astigmatic axis angle and at an angle orthogonal thereto.

Figure 15:
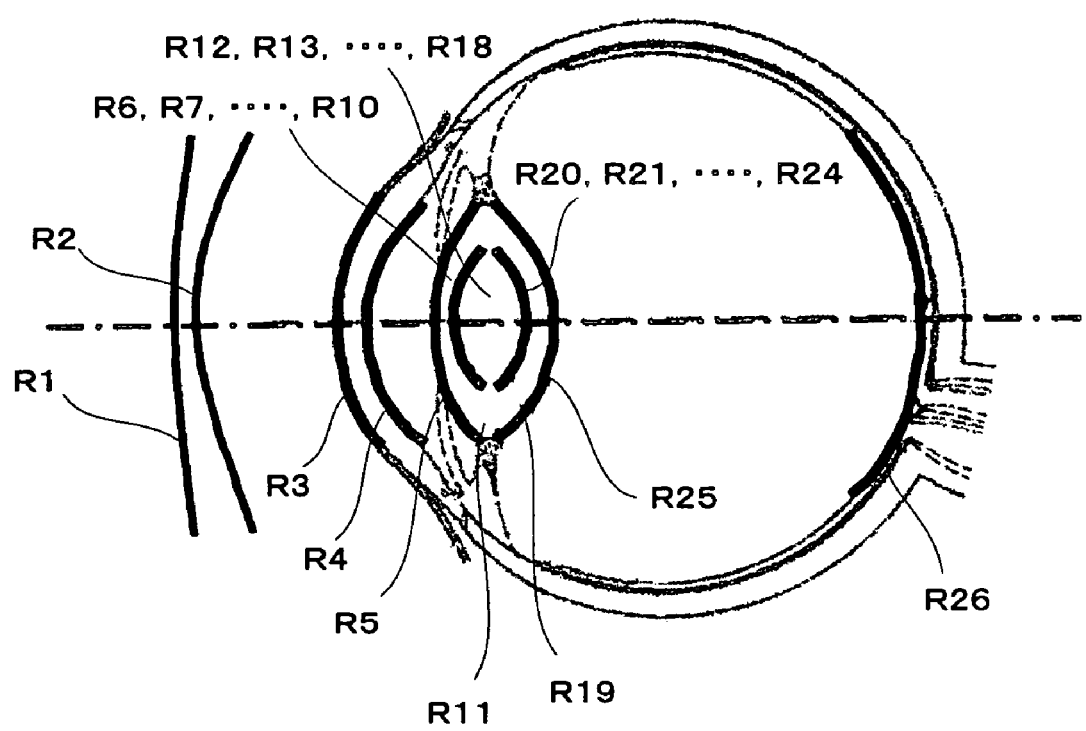
FIG. 15 is a conceptual view showing an optical eyeball model used in the optometric apparatus according to a preferred embodiment of the present invention.
Figure 16:
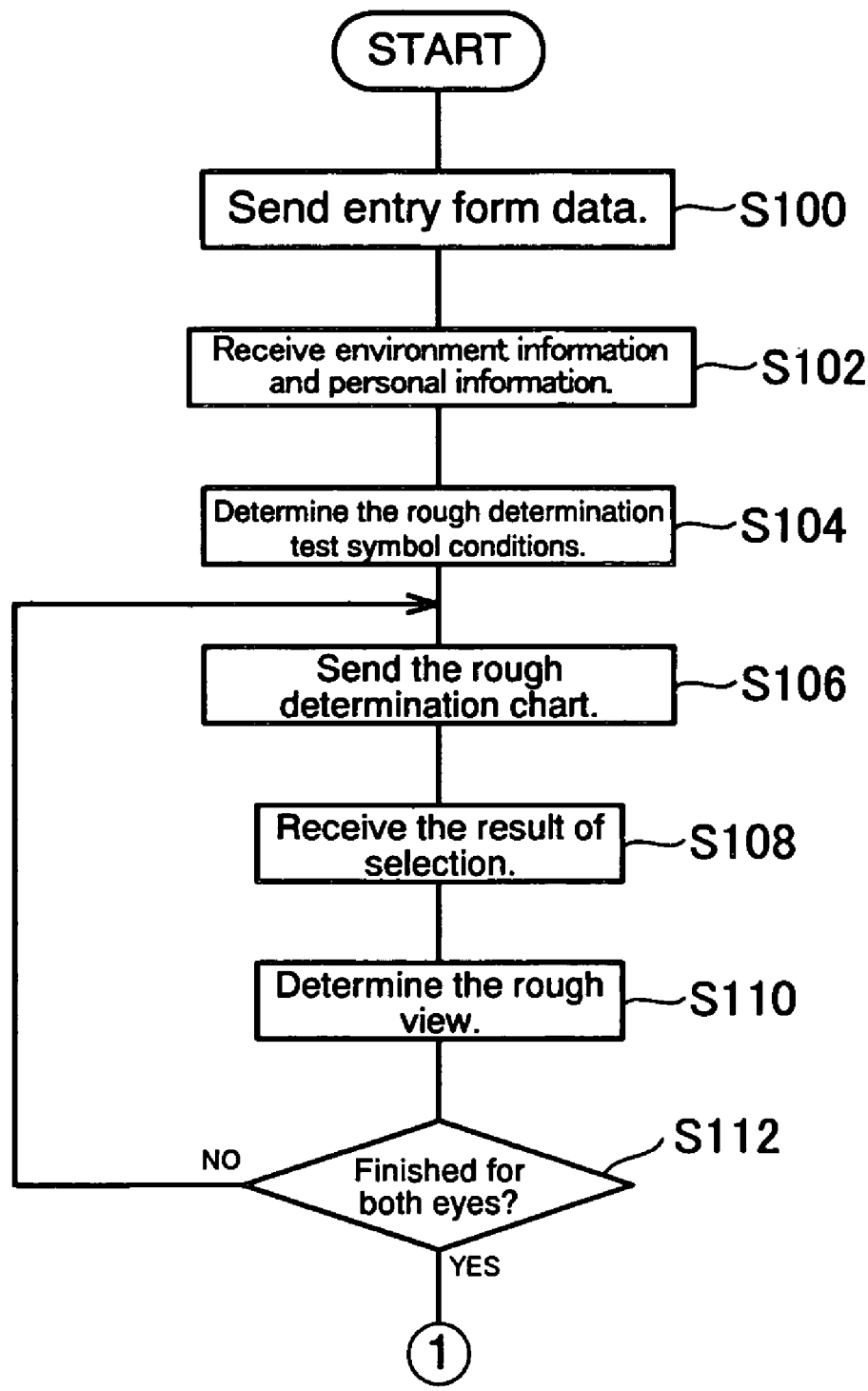
FIG. 16 is a process flow diagram (for personal information collection processing and rough determination processing) in the optometric apparatus according to a preferred embodiment of the present invention.
Figure 17:
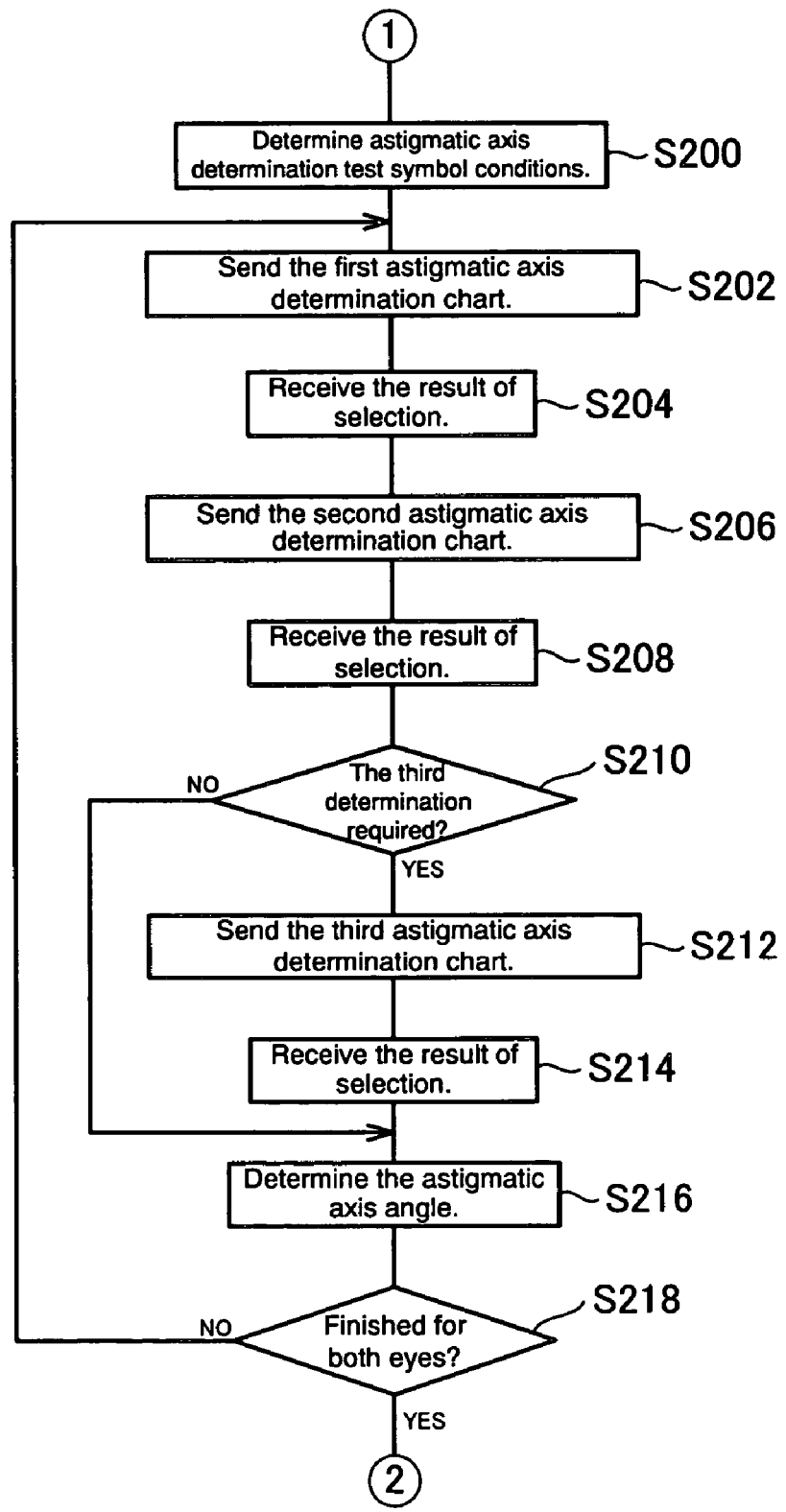
FIG. 17 is a process flow diagram (for astigmatic axis determination processing) in the optometric apparatus according to a preferred embodiment of the present invention.
Figure 18:
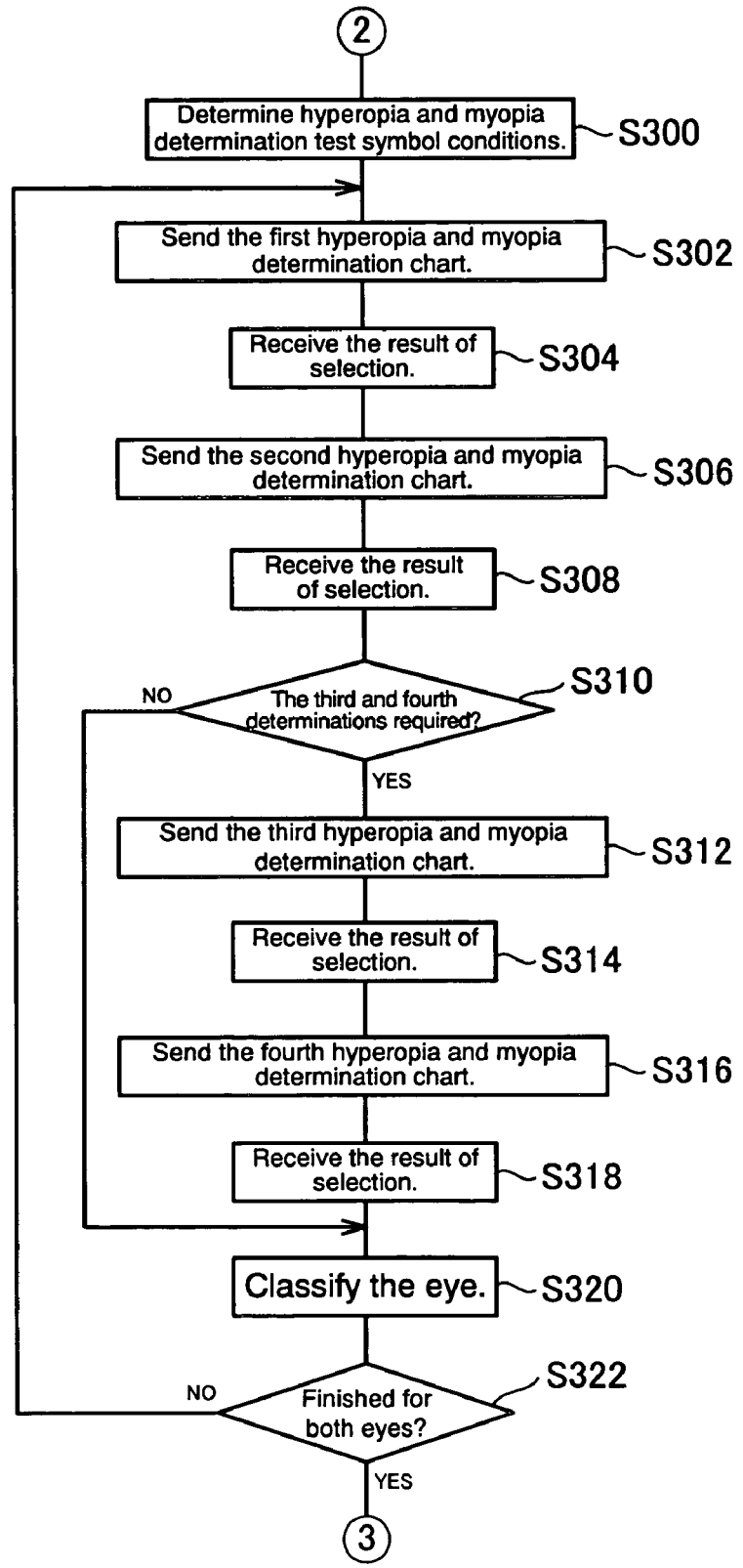
FIG. 18 is a process flow diagram (for hyperopia and myopia determination processing) in the optometric apparatus according to a preferred embodiment of the present invention.
Figure 19:
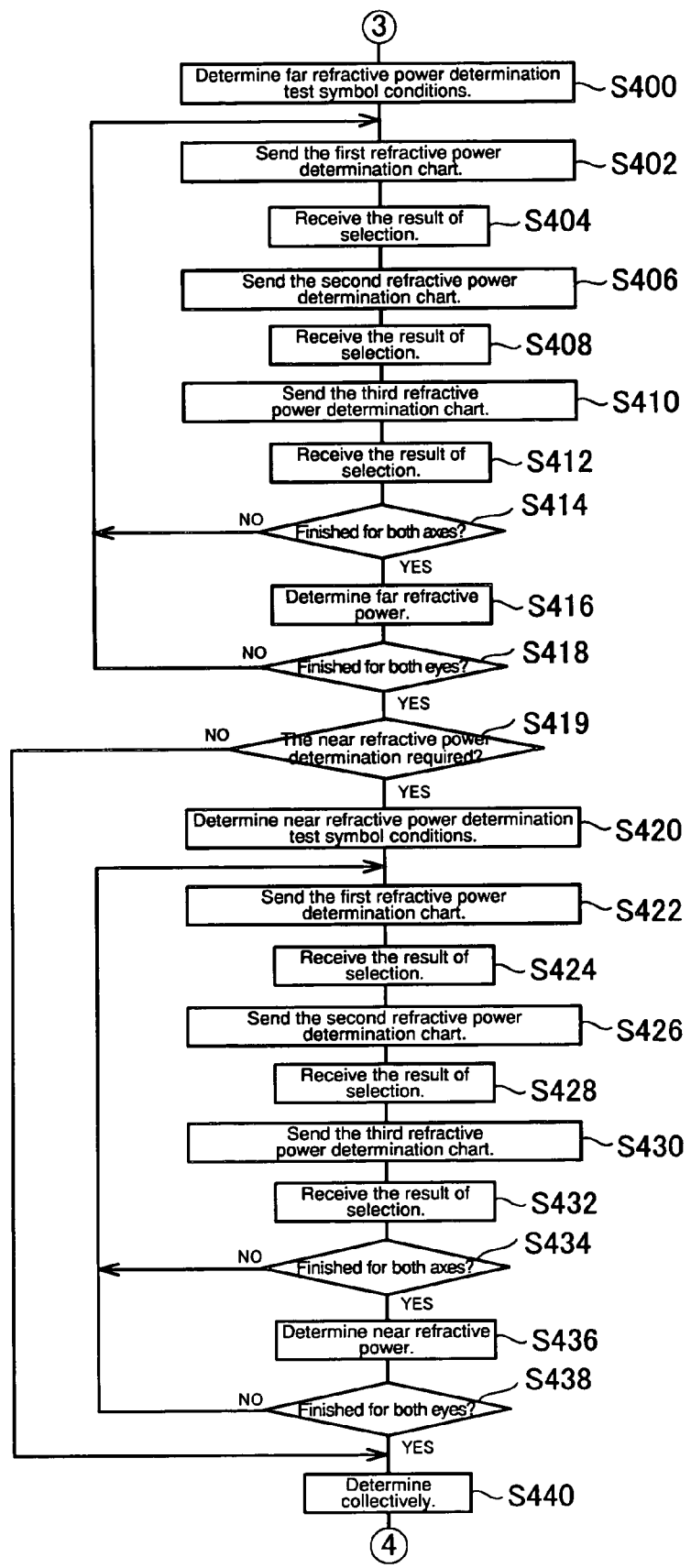
FIG. 19 is a process flow diagram (for refractive power determination processing) in the optometric apparatus according to a preferred embodiment of the present invention.
Figure 20:
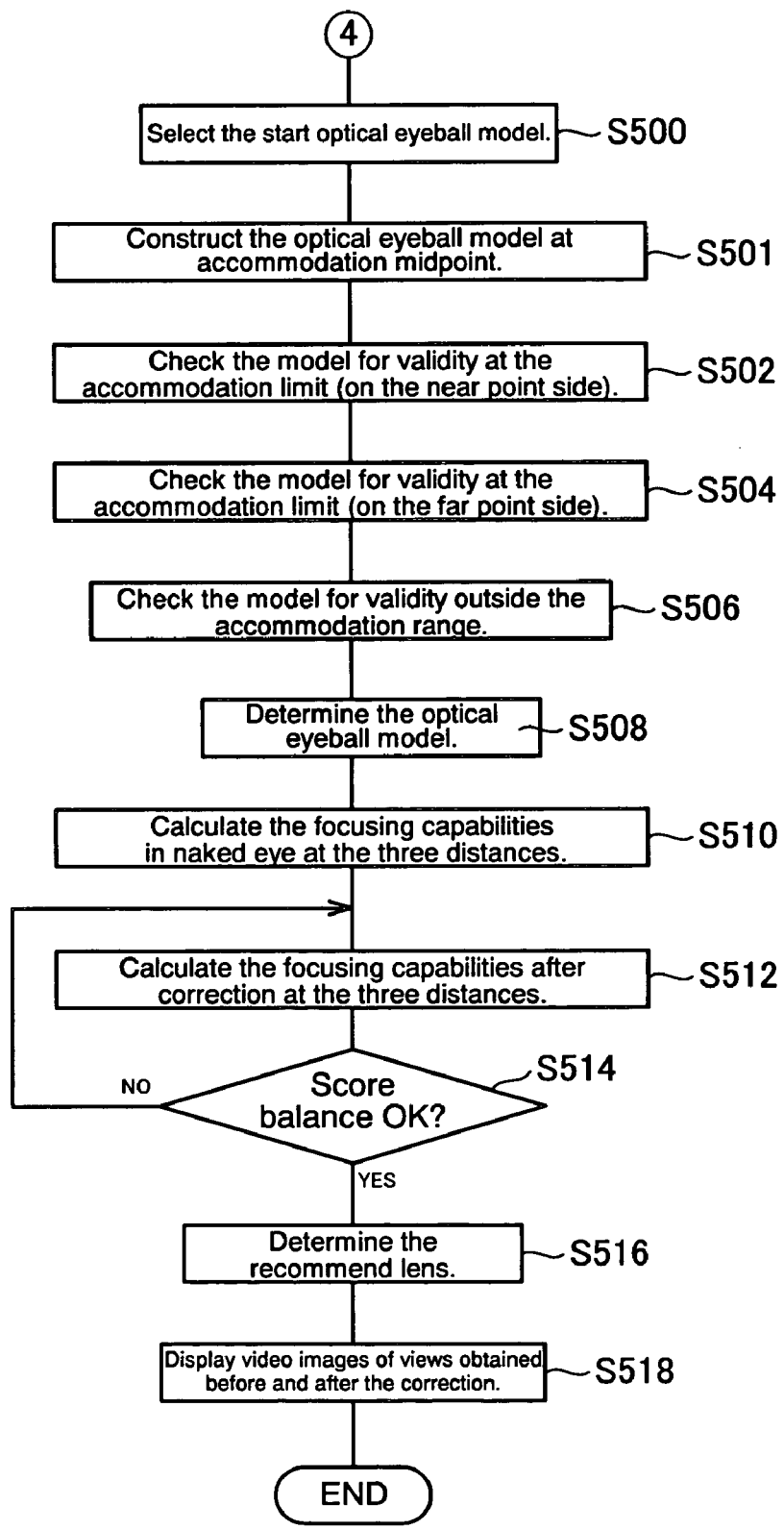
FIG. 20 is a process flow diagram (for lens power determination processing) in the optometric apparatus according to a preferred embodiment of the present invention.
Figure 21:
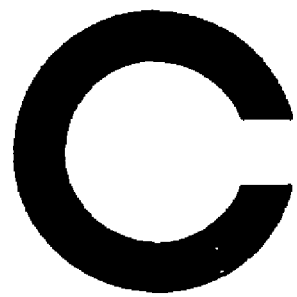
FIG. 21 is a view showing an example of a conventional test symbol (Landoldt ring) for use in determination of visual acuity.
Figure 21:
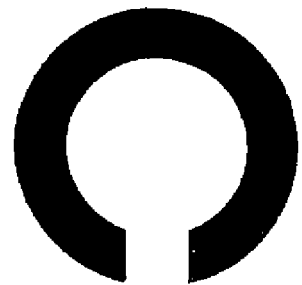
Figure 21:
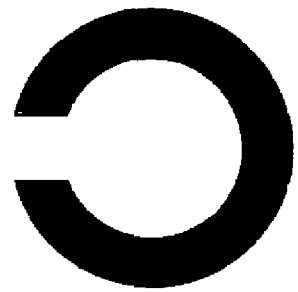
Figure 21:
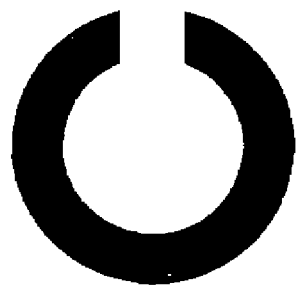
Figure 22:
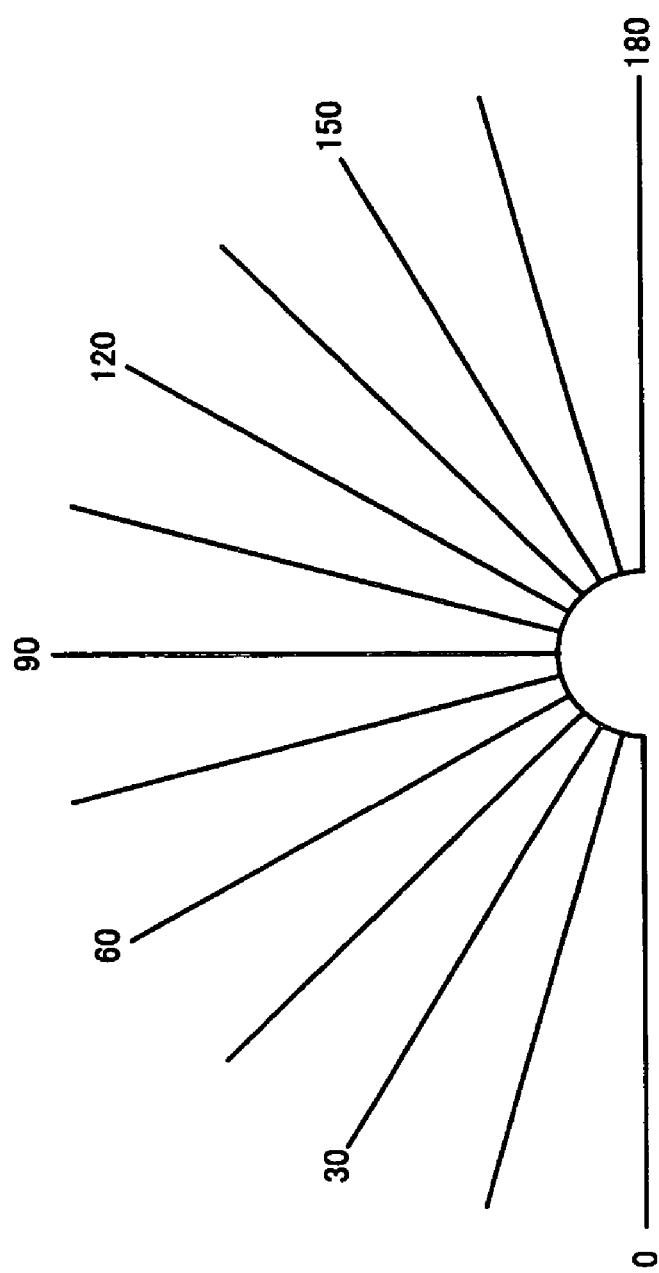
FIG. 22 is a view showing an example of a conventional test symbol for use in determination of astigmatic axes.

The optical eyeball model determination means 30 is designed to select a start optical eyeball model based on the age class and the approximate refractive power. As used herein, the start optical eyeball model includes the age class represented on the vertical axis and the refractive power class represented on the horizontal axis, in which an optical eyeball model is created in advance with the median of the respective classes. Thus, the optical eyeball model determination means 30 includes a start optical eyeball model database (not shown), which stores an optical eyeball model with the age class represented on the vertical axis and the refractive power represented on the horizontal axis, at the accommodation limit on the far point side in each class and an optical eyeball model defined at the accommodation limit on the near point side by assuming that the power of accommodation depends on the age. Thus, with the vertical axis representing M classes and the horizontal axis representing N classes, a total of 2 times M times N start optical eyeball models are stored. An optical eyeball model determined by the optical eyeball model determination means 30 simulates the human eye by means of the lens system as shown in FIG. 15.

The subject terminal 50, which is used for the subject to take an eye examination, is located at home or in shops for communicating various data with the eye examination server 12 via the network 100. The subject terminal 50 used is a computer, such as a personal computer or a workstation, which includes an input device such as a keyboard or mouse.

The subject terminal 50 includes a WWW browser (not shown) for accessing the eye examination server 12, and is linked to the WWW server 16 by entering the IP address or URL, assigned to the eye examination server 12, to the URL entry field, thereby allowing the subject to take eye examination service. The WWW browser displays the image of the test symbols received from the WWW server 16 and sends the result of determination entered by the subject to the WWW server 16.

As used herein, the Internet is used as the network 100 in order to perform the eye examination. However, any network may be used as long as the network provides two-way data communications. Suitable networks include a public telephone network, an ISDN network, a cellular telephone network, and dedicated networks.

Now, with reference to the process flowcharts shown in FIGS. 16 to 20, the operation of the eye examination server 12 will be explained below which is performed when the subject accesses the eye examination server 12 using the WWW browser at the subject terminal 50.

First, the eye examination server 12 sends to the subject terminal an entry form in which the environment information such as the size and resolution of the screen of the subject terminal and the personal information such as the name, age, and height of the subject are entered (S100). This operation allows the entry form to be displayed on the screen of the subject terminal. The subject then enters data into the input form and clicks on the "Send" button, thereby causing the eye examination server 12 to receive the environment information and the personal information (S102).

Then, the eye examination server 12 performs the rough view determination processing in S104 to S112.

First, the server 12 determines the test symbol conditions for the rough view determination in accordance with the environment information and personal information received (S104).

The server 12 then sends to the subject terminal the rough view determination chart having a combination of test symbols 22*a* selected in accordance with the test symbol conditions determined (S106). This allows the rough view determination chart, as shown in FIG. 2, to be displayed on the screen of the subject terminal. On the screen, the subject views the rough view determination chart displayed at the subject's reach, with either one of the right and left eyes, and then clicks on the smallest test symbol readable as "8." When all of the test symbols cannot be read as "8," the subject clicks on the display part showing "All unreadable." This allows the eye examination server 12 to receive the result selected through the rough view determination by the subject (S108) and then determine the rough view of the subject based on the size of the test symbol selected (the view number) (S110).

This processing is performed on both the right and left eyes (S112), and then the server 12 terminates the rough view determination processing.

Then, the eye examination server 12 performs the astigmatic axis determination processing in S200 to S218.

First, the server 12 determines the test symbol conditions for the astigmatic axis determination in accordance with the received environment information, personal information, and the view number obtained through the rough view determination processing (S200).

Figure 3:
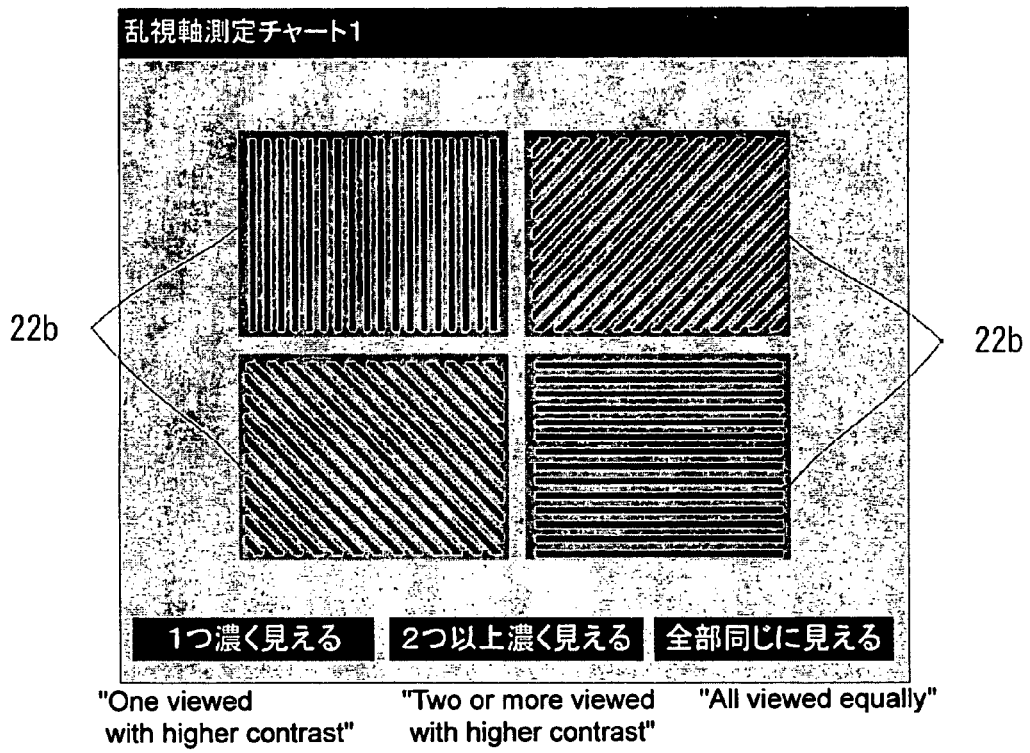
FIG. 3 is a view showing an example of a first astigmatic axis determination chart.

Then, the server 12 sends to the subject terminal the first astigmatic axis determination chart having a combination of test symbols oriented at angles of about 45 degrees, about 90 degrees, about 135 degrees, and about 180 degrees, in accordance with the determined test symbol conditions (S202). This allows the chart, as shown in FIG. 3, to be displayed on the screen of the subject terminal. The subject moves closer to the screen until any one of the test symbols in the displayed chart can be viewed clearly, and then views the chart with either one of the right and left eyes to determine which test symbol is viewed with greater contrast. When one test symbol is viewed with greater contrast, then the subject clicks the display part showing "One viewed with greater contrast" and then on the test symbol viewed with greater contrast. When two or more test symbols are viewed with greater contrast, the subject clicks on the display part "Two or more viewed with greater contrast" and then on the test symbols viewed with greater contrast in order of greater contrast. When all test symbols are viewed equally, the subject clicks on the display part "All viewed equally." This allows the eye examination server 12 to receive the results selected through the first astigmatic axis determination by the subject (S204).

Figure 4:
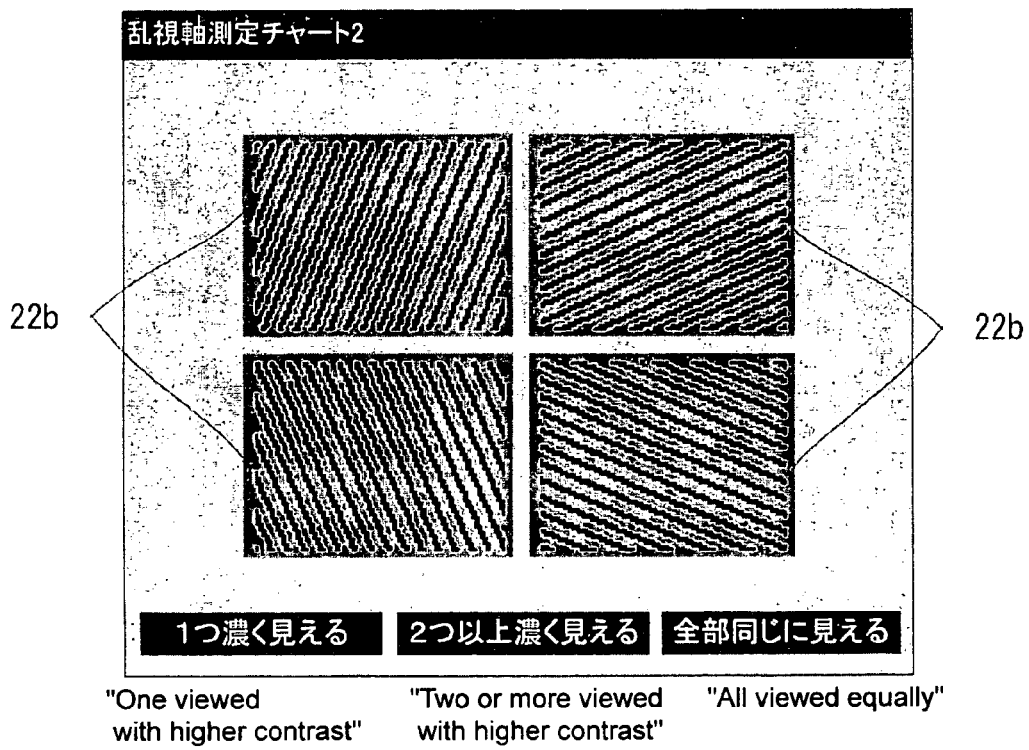
FIG. 4 is a view showing an example of a second astigmatic axis determination chart.

Then, the server 12 sends to the subject terminal the second astigmatic axis determination chart having a combination of test symbols oriented at angles of 23 degrees, 68 degrees, 113 degrees, and 158 degrees, in accordance with the determined test symbol conditions (S206). This allows the chart, as shown in FIG. 4, to be displayed on the screen of the subject terminal. The subject moves closer to the screen until any one of the test symbols in the chart displayed can be viewed clearly, and then views the chart with either one of the right and left eyes to determine which test symbol is viewed with greater contrast and clicks thereon. This allows the eye examination server 12 to receive the results selected through the second astigmatic axis determination by the subject (S208).

Figure 5:
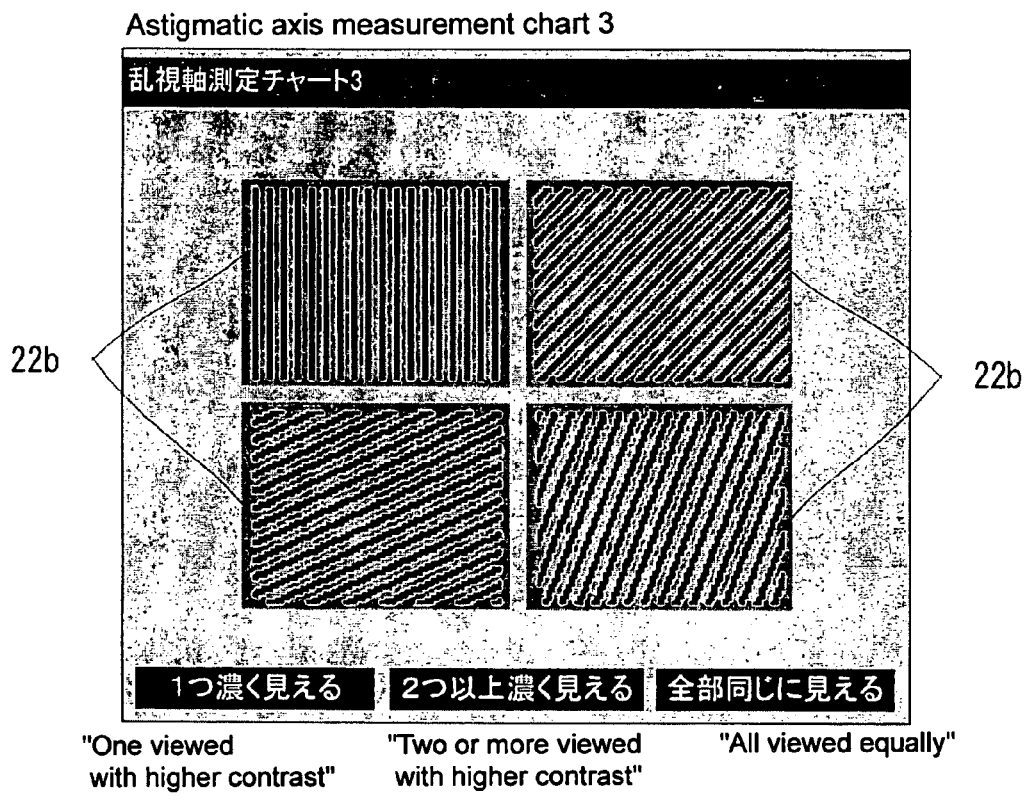
FIG. 5 is a view showing an example of a third astigmatic axis determination chart (No.1)
Figure 6:
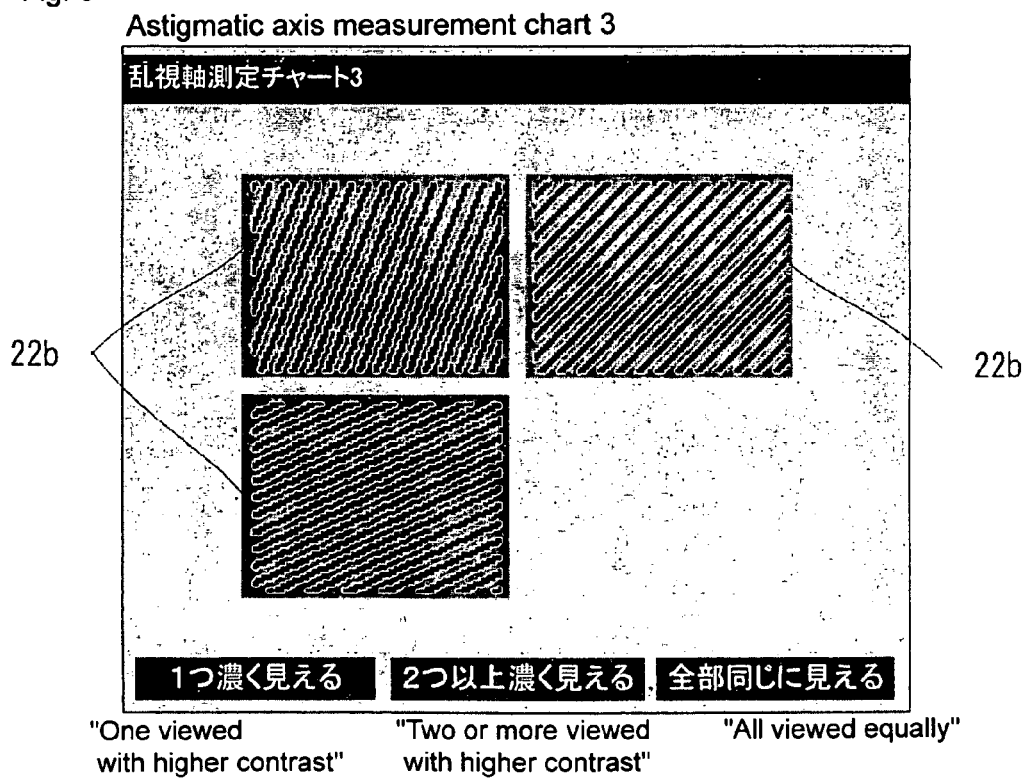
FIG. 6 is a view showing an example of a third astigmatic axis determination chart (No.2)
Figure 7:
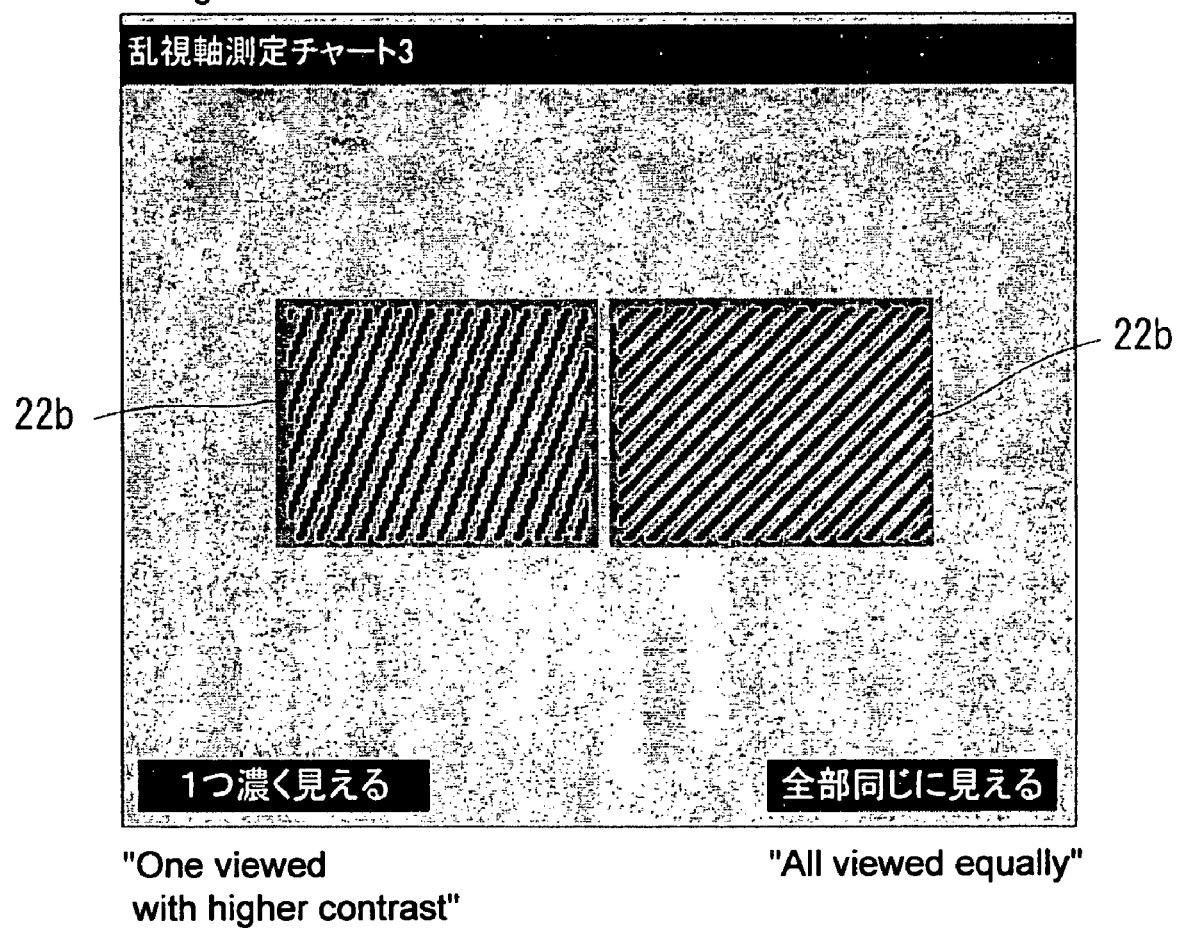
FIG. 7 is a view showing an example of a third astigmatic axis determination chart (No.3)

Then, in accordance with the results selected through the first astigmatic axis determination and the second astigmatic axis determination, it is determined whether or not the third astigmatic axis determination should be performed (S210). Here, the third astigmatic axis determination is to be performed when "All viewed equally" has not been selected in any of the first astigmatic axis determination and the second astigmatic axis determination. To perform the third astigmatic axis determination, the server 12 sends to the subject terminal the third astigmatic axis determination chart having a combination of the test symbol selected in the first astigmatic axis determination and the test symbol selected in the second astigmatic axis determination (S212). This allows the charts, as shown in FIGS. 5 to 7, to be displayed on the screen of the subject terminal. In this manner, the third astigmatic axis determination chart is appropriately created as any one of the representations of two selected test symbols, three selected test symbols, and four selected test symbols. The subject moves closer to the screen until any one of the test symbols displayed in the chart can be viewed clearly and then views the charts with either one of the right and left eyes to determine which test symbol is viewed with greater contrast and clicks thereon as described above. This allows the eye examination server 12 to receive the results selected through the third astigmatic axis determination by the subject (S214).

Finally, the server 12 determines the astigmatic axis angle of the subject based on the results selected in each chart (S216). The algorithm of the determination is as follows.

The combinations of the selected test symbols in each astigmatic axis determination chart are divided into the eleven cases as shown in Table 1.

TABLE 1

| Case No. | Selection in the first chart | Selection in the second chart | Test symbol presented in the third chart | Selection in the third chart |
|---|---|---|---|---|
| 1 | Same for all | Same for all | None | None |
| 2 | Same for all | One | None | None |
| 3 | Same for all | Two | None | None |
| 4 | One | Same for all | None | None |
| 5 | One | One | Two | One, Equally viewed |
| 6a | One | Two | Three | One, Two, Equally viewed |
| 6b | One | Two | None | None |
| 7 | Two | Same for all | None | None |
| 8a | Two | One | Three | One, Two, Equally viewed |
| 8b | Two | One | None | None |
| 9 | Two | Two | Four | One, Two, Equally viewed |

In the case of the angle of a test symbol selected in the first stigmatic axis determination chart being greatly different from that of a test symbol selected in the second astigmatic axis determination chart, the eye examination server 12 acknowledges this case as an error because the data is unreliable. The cases acknowledged as an error have case numbers 5, 6, 8, and 9, and the determination of error is made depending on the condition expressed by Equation 1 being satisfied or not. If a case satisfies the condition, the case is treated as an error, thus allowing the determination to be interrupted or redone.

$$50 < |A_{1m} - A_{2m}| < 130 \qquad \text{Equation 1}$$

In Equation 1, $A_{1m}$ is the average of angles of the test symbols selected in the first astigmatic axis determination chart or when one test symbol has been selected $A_{1m}$ is the angle of the test symbol. $A_{2m}$ is the average of angles of the test symbols selected in the second astigmatic axis determination chart or when one symbol has been selected $A_{2m}$ is the angle of the test symbol.

The eye examination server 12 performs processing as follows on each case in Table 1 to determine the astigmatic axis angle.

(1) Case No. 1: No astigmatism is determined to be present.

(2) Case No. 2: The angle of the test symbol selected in the second astigmatic axis determination chart is determined to be the astigmatic axis angle.

(3) Case No. 3: The average of the angles of two test symbols selected in the second astigmatic axis determination chart is determined to be the astigmatic axis angle.

(4) Case No. 4: The angle of a test symbol selected in the first astigmatic axis determination chart is determined to be the astigmatic axis angle.

(5) Case No. 5: When one test symbol is selected in the third astigmatic axis determination chart, the angle of the test symbol is determined to be the astigmatic axis angle. When "Viewed equally" is selected, the average of the angles of two test symbols is determined to be the astigmatic axis angle.

(6) Case No. 6a: When one test symbol is selected in the third astigmatic axis determination chart, the angle of the test symbol is determined to be the astigmatic axis angle. When two test symbols are selected, the average of the angles of the two test symbols selected is determined as the astigmatic axis angle. When "Viewed equally" is selected, it is assumed that the selection is made by mistake and thus an error is acknowledged.

(7) Case No. 6b: When the angle of a test symbol selected in the first astigmatic axis determination chart is equal to the average of the angles of two test symbols selected in the second astigmatic axis determination chart, the angle of the test symbol selected in the first astigmatic axis determination chart is determined to be the astigmatic axis angle.

(8) Case No. 7: The average of the angles of two test symbols selected in the first astigmatic axis determination chart is determined to be the astigmatic axis angle.

(9) Case No. 8a: When one test symbol is selected in the third astigmatic axis determination chart, the angle of the test symbol is determined to be the astigmatic axis angle. When two test symbols are selected, the average of the angles of the two test symbols selected is determined as the astigmatic axis angle. When "Viewed equally" is selected, it is assumed that the selection is made my mistake and thus an error is acknowledged.

(10) Case No. 8b: When the angle of a test symbol selected in the second astigmatic axis determination chart is equal to the average of the angles of two test symbols selected in the first astigmatic axis determination chart, the angle of the test symbol selected in the second astigmatic axis determination chart is determined to be the astigmatic axis angle.

(11) Case No. 9: When one test symbol is selected in the third astigmatic axis determination chart, the angle of the test symbol is determined to be the astigmatic axis angle. When two test symbols are selected, the average of the angles of the two test symbols selected is determined as the astigmatic axis angle. When "Viewed equally" is selected, no astigmatism is determined to be present.

The aforementioned processing makes it possible to determine the astigmatic axis angle with twice the resolution of the increments of angle used.

The aforementioned processing is performed on the right and left eyes (S218), and then the flow terminates the astigmatic axis determination processing.

Then, the eye examination server 12 performs the hyperopia and myopia determination processing in S300 to S324.

First, the server 12 determines the test symbol conditions for the hyperopia and myopia determination in accordance with the environment information and the personal information received, the view number obtained through the rough determination processing, and the astigmatic axis angle determined through the astigmatic axis determination processing (S300).

The size of the test symbols and the width and intervals of the straight lines presented are varied as shown in Table 2 depending on the view number obtained through the rough determination processing. As the view number increases, the size of the test symbols as well as the width and interval of the black lines are increased in this manner. Since higher degrees of myopia will cause the appearance of the red color to diffuse thereby making the black lines more obscure, the ratio between the width and intervals of the black lines is increased with increasing view numbers.

TABLE 2

| Views Of "8" | Rough degree of Myopia | Line width (Pixel) | Width of areas between the lines (Pixel) | Test symbol size (Pixel) |
| --- | --- | --- | --- | --- |
| 1, 2 | −1.5 dpt | 2 | 3 | 220 × 140 |
| 3, 4 | −3.0 dpt | 6 | 6 | 380 × 220 |
| 5, 6 | −5.5 dpt | 20 | 10 | 470 × 270 |
| 7, None viewable | −9.0 dpt | 60 | 20 | 560 × 330 |

The straight lines of the presented test symbols are displayed, as a rule, at an astigmatic axis angle and at angle orthogonal thereto. However, since no hyperopia and myopia determination test symbols are prepared in the central orientations in increments of 23 degrees as described above, the test symbols which are drawn at one of the angles in increments of 23 degrees that is closest to the astigmatic axis determined and at an angle orthogonal thereto are used.

Then, the server 12 sends to the subject terminal the first hyperopia and myopia determination chart having the straight lines drawn at the angle selected in accordance with the astigmatic axis angle in both the red and blue areas (S302). This allows the chart, as shown in FIG. 8(a), to be displayed on the screen of the subject terminal. On the screen, the subject views the displayed chart with either one of the right and left eyes at the subject's reach to determine which straight lines either in the red or blue area are viewed clearly. Then, the subject clicks either on the clearly viewed area or on "Both viewed equally." This allows the eye examination server 12 to receive the result selected through the first hyperopia and myopia determination by the subject (S304).

Then, the server 12 sends to the subject terminal the second hyperopia and myopia determination chart having the straight lines drawn in both the red and blue areas at an angle orthogonal to the angle selected in accordance with the astigmatic axis angle (S306). This allows the chart, as shown in FIG. 8(b), to be displayed on the screen of the subject terminal. On the screen, the subject views the displayed chart with either one of the right and left eyes at the subject's reach to determine, in the same manner as in the foregoing, which straight lines either in the red or blue area are viewed clearly and clicks thereon. This allows the eye examination server 12 to receive the results selected through the second hyperopia and myopia determination by the subject (S308).

Then, in accordance with the results selected through the first hyperopia and myopia determination and the second hyperopia and myopia determination, it is determined whether or not the third hyperopia and myopia determination and the fourth hyperopia and myopia determination are to be performed (S310). Here, the third hyperopia and myopia determination and the fourth hyperopia and myopia determination are to be performed when the subject is determined to have hyperopia in any of the first hyperopia and myopia determination and the second hyperopia and myopia determination.

Figure 8:
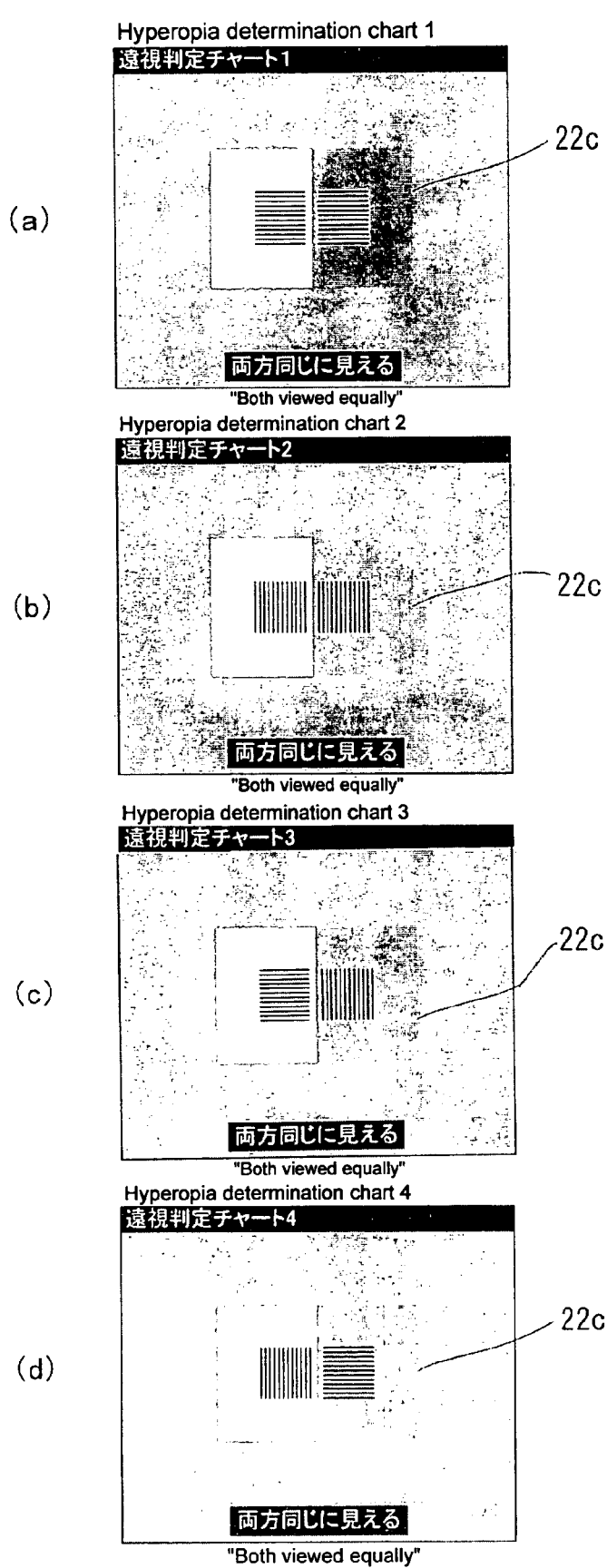
FIG. 8 is a view showing an example of a hyperopia and myopia determination chart.

To perform the third hyperopia and myopia determination and the fourth hyperopia and myopia determination, the server 12 sends to the subject terminal the third hyperopia and myopia determination chart which includes straight lines drawn in the red area at an angle selected in accordance with the astigmatic axis angle and which includes straight lines drawn in the blue area at an angle orthogonal thereto (S312). This allows the chart, as shown in FIG. 8(c), to be displayed on the screen of the subject terminal. On the screen, the subject views the displayed chart with either one of the right and left eyes at the subject's reach to determine, in the same manner as in the foregoing, which straight lines either in the red or blue area are viewed clearly and clicks thereon. This allows the eye examination server 12 to receive the result selected through the third hyperopia and myopia determination by the subject (S314). Additionally, the server 12 sends to the subject terminal the fourth hyperopia and myopia determination chart which includes straight lines drawn in the blue area at an angle selected in accordance with the astigmatic axis angle and which includes straight lines drawn in the red area at an angle orthogonal thereto (S316). This allows the chart, as shown in FIG. 8(*d*), to be displayed on the screen of the subject terminal. On the screen, the subject views the displayed chart with either one of the right and left eyes to determine, in the same manner as in the foregoing, which straight lines either in the red or blue area are viewed clearly and clicks thereon. This allows the eye examination server to receive the results selected through the fourth hyperopia and myopia determination by the subject (S318).

Then, the subject's eye is classified (determined) into either hyperopia or myopia in accordance with the results selected in the four hyperopia and myopia determination charts (S320). Now, a detailed explanation is given below as to how the eye is classified. The selections made in the four hyperopia and myopia determination charts can be classified into the eleven cases as shown in Table 3.

tion. If the collective determination is reliable, both of the axes are determined to exhibit hyperopia or myopia, whereas if not, both the axes are determined to be indeterminate.

The aforementioned processing is performed on both the right and left eyes (S322), and then the flow terminates the hyperopia and myopia determination processing.

Subsequently, the eye examination server 12 performs the refractive power determination processing in S400 to S440. As described above, only the far refractive power determination processing for determining the refractive power at the subject's reach is usually performed for the refractive power determination. In a particular case, the near refractive power determination processing for determining the refractive power at an A4-sized-paper distance is performed as an additional processing for a collective determination.

First, the far refractive power determination processing determines the test symbol conditions for the far refractive power determination in accordance with the environment information and the personal information received, the view number obtained through the rough determination processing, and the astigmatic axis angle determined through the astigmatic axis determination processing (S400). The angle of the test symbols displayed is, as a rule, the determined astigmatic axis angle and an angle orthogonal thereto. However, since the refractive power determination test symbols are drawn only at angles in increments of 45 degrees as described above, the test symbols which are drawn at one of

TABLE 3

| Case No. | Selection in (a) | Selection in (b) | Selection in (c) | Selection in (d) | Determination at 90 deg axis | Determination at 180 deg axis | Remarks |
|---|---|---|---|---|---|---|---|
| (1) | Red | Red | Red | Red | Myopia | Myopia | |
| (2) | Red | Red | Same | Red | Myopia | Myopia (Pending) | |
| (3) | Red | Red | Red | Same | Myopia | Myopia (Pending) | |
| (4) | Red | Same | Red | Red | Myopia (Pending) | Myopia | |
| (5) | Same | Red | Red | Red | Myopia (Pending) | Myopia | |
| (6) | Blue | Blue | Blue | Blue | Hyperopia | Hyperopia | |
| (7) | Blue | Same | Blue | Blue | Hyperopia | Hyperopia | Other Combination with "Blue" and "Same" |
| (8) | Red | Red | Blue | Red or Blue or Same | Myopia | Hyperopia (Pending) | |
| (9) | Red | Blue | Blue | Red or Blue or Same | Myopia (Pending) | Hyperopia | |
| (10) | Blue | Red or Blue or Same | Red | Blue | Hyperopia | Myopia (Pending) | |
| (11) | Blue | Red or Blue or Same | Red | Red | Hyperopia (Pending) | Myopia | |

In Table 3, case No. 1 shows that "red" is selected for all the test symbols, and thus, both of the astigmatic axis angle and the angle orthogonal thereto are determined to exhibit myopia. Case Nos. 6 and 7 show that "blue" for all or either "blue" or "Viewed equally" is selected, and thus, both axes are determined to exhibit hyperopia. In other case Nos. in which "Viewed equally," "red," and "blue" are selected in combination, the determination is divided into either to be made for both axes at the spot or to be suspended depending on the result of selection. In the case of the determination being suspended, the result is retained and will be used for a collective determination in conjunction with the result of a far refractive power determination that subsequently follows as well as with the result of a near refractive power determinathe angles in increments of 45 degrees that is closest to the astigmatic axis determined and at an angle orthogonal thereto are used. Accordingly, in the cases of no astigmatism, astigmatism with the rule, and astigmatism against the rule, the determination is to be made on the test symbols drawn at angles of 90 degrees and 180 degrees, whereas in the case of heterotropia, a check is made on the test symbols drawn at angles of 45 degrees and 135 degrees.

If the astigmatic axis angle of the subject and the angle orthogonal thereto are different from the angle of the test symbol by 15 degrees or more, determinations may be made on all the test symbols drawn at angles of about 90 degrees, about 180 degrees, about 45 degrees, and about 135 degrees to weigh the results, thereby determining the refractive powers at the astigmatic axis angle and at an angle orthogonal thereto. This makes it possible to determine refractive powers with improved accuracy using only a limited number of test symbol orientations.

The test symbols are displayed at a size of about four times the refractive powers (in diopters) within the measurement range. The sizes of the test symbols are limited to about 9 to 18 ranges according to the view number, and divided into three groups, such that each group has a combination of test symbols different in size by three steps for use.

Then, the server 12 sequentially sends to the subject terminal the combinations of test symbols of the respective three groups in the first far refractive power determination chart, the second far refractive power determination chart, and the third far refractive power determination chart (S402, S406, and S410). This allows the charts, as shown in FIGS. 10, 11, and 12, respectively, to be displayed on the screen of the subject terminal. On the screen, the subject views the displayed charts with either one of the right and left eyes at the subject's reach to determine the smallest test symbol that provides a clear appearance of three straight lines in each chart and then click thereon. When none of the test symbols are viewed with three straight lines, the subject clicks on "None appearing with 3 lines." This allows the eye examination server 12 to receive the results selected by the subject (S404, S408, and S412). This is done on the selected angle and the angle orthogonal thereto (S414). Then, the server 12 checks the results selected in the three charts with each other to determine the far refractive power (S416). Now, an explanation is given to the processing for determining the far refractive power based on the results selected in the three charts.

First, the test symbols selected in the three charts are arranged in order of size to determine whether there is a combination of adjacent test symbols having a minimum step difference of one. For example, when No. 4, No. 5, and No. 6 have been selected in the first, second, and third charts, respectively, the combination of the adjacent targets has a minimum step difference of one. In this case, it is determined that the subject has selected, without any error, the test symbols which are clearly viewed in the three charts. Then, the smallest one of the test symbols, i.e., No. 4 is determined to exhibit the refractive power. On the other hand, if the test symbols selected in the three charts have no combination of a minimum step difference of one, the determination is made in the subsequent step.

Now, the test symbols selected in the three charts are arranged in order of size to determine whether there is a combination of adjacent test symbols having a minimum step difference of two. For example, suppose that No. 4, No. 8, and No. 6 have been selected in the first, second, and third charts, respectively. In this case, when the test symbols selected in the three charts are arranged in order of size, the combination of the adjacent targets has a minimum step difference of two. With such a result, it is determined that any one of the test symbols selected in the three charts possibly has been entered by mistake. In this case, the average of size of the two smaller ones of the far test symbols selected (No. 5 in this case) is determined to exhibit the smallest test symbol clearly viewed by the subject, thereby determining the refractive power.

Then, for the suspended classifications in the hyperopia and myopia determination processing, the eye classification is reviewed in accordance with the age of the subject and the test symbol calculated in the far refractive power determination. If no determination can be made, those which seem to be possibly determined later in the near refractive power determination are suspended, whereas the remainder is determined to be indeterminate and thus as an error, or is re-measured.

The aforementioned processing is performed on both the right and left eyes (S418), and then the flow terminates the far refractive power determination processing.

Then, the eye examination server 12 determines whether the "near refractive power determination" needs to be additionally performed (S419). This additional processing needs to be performed on all the subjects for whom the eye classification has been suspended and on all the subjects of the age of 40 or older with hyperopia. This is because some people with hyperopia or presbyopia have a reach longer than the near point distance and are within the range of accommodation, and thus, the refractive power cannot be determined by only the far refractive power determination.

To perform the near refractive power determination processing, the server 12 determines the test symbol conditions for the near refractive power determination in accordance with the astigmatic axis angle determined through the astigmatic axis determination processing, the test symbol number obtained through the far refractive power determination, and the age (S420).

The astigmatism with the rule and astigmatism against the rule are determined on the test symbols presented both at angles of 90 degrees and 180 degrees or at either one thereof. In the case of heterotropia, the determination is made at angles of (1) either about 45 degrees or about 135 degrees; (2) both about 45 degrees and about 135 degrees; (3) either about 45 degrees or about 135 degrees and either about 90 degrees or about 180 degrees; or (4) both about 45 degrees and about 135 degrees or both about 90 degrees and about 180 degrees. In this case, the determination is made on those subjects whose eye classification has been suspended, according to (2) or (4) above, whereas the determination is made on those subjects whose eye classification has already been determined, according to (1) and (3) above.

As in the far refractive power determination, the sizes of the test symbols presented are limited to about 9 to 18 ranges according to the view number within their entire range of size, and divided into three groups of sizes in which a combination of test symbols in which the step difference in size is three.

Then, the server 12 sequentially sends to the subject terminal the combinations of test symbols of the respective three groups in the first near refractive power determination chart, the second near refractive power determination chart, and the third near refractive power determination chart (S422, S426, and S430). The subject views the respective charts displayed with either one of the right and left eyes at an A4-paper distance to determine the smallest test symbol that provides a clear appearance of three straight lines in each chart and clicks thereon. When none of the test symbols are viewed with three lines, the subject clicks on "None viewed with 3 lines." This allows the eye examination server 12 to receive the results selected by the subject (S424, S428, and S432). This is done at the selected angle and at the angle orthogonal thereto (S434). Then, in the same procedure as in the far refractive power determination, the server 12 checks the results selected in the three charts with each other to determine the near refractive power (S436). The processing for determining the near refractive power is performed in the same manner as the processing for determining the far refractive power described above. At this time, for the suspended classifications in the hyperopia and myopia determination processing, the eye classification is reviewed in accordance with the age of the subject, the refractive power calculated in the far refractive power determination, and the refractive power calculated in the near refractive power determination. This is done in the following procedure.

(1) The difference between the results of the far refractive power determination and the near refractive power determination at the astigmatic axis angle and at an angle orthogonal thereto is calculated.

$$SA1 = F1 - N1, \text{ and}$$

$$SA2 = F2 - N2$$

where F1 is the far refractive power determination test symbol at the astigmatic axis angle, N1 is the near refractive power determination test symbol at the astigmatic axis angle, F2 is the far refractive power determination test symbol at an angle orthogonal to the astigmatic axis angle, and N2 is the near refractive power determination test symbol at an angle orthogonal to the astigmatic axis angle.

(2) Determination of Myopia

Myopia is defined as the near refractive power determination providing a better view than the far refractive power determination in the presence of a specific difference in test symbol number between the far refractive power determination test symbol and the near refractive power determination test symbol. Accordingly, with $SA1 \geqq 0$, $SA2 \geqq 0$, and $SA1 + SA2 \geqq 6$, both the axes are determined to exhibit myopia.

(3) Determination of Hyperopia

Hyperopia is defined as the far refractive power determination providing a better view than the near refractive power determination in the presence of a specific difference in test symbol number between the far refractive power determination test symbol and the near refractive power determination test symbol. Accordingly, with $SA1 \leqq 0$, $SA2 \leqq 0$, and $SA1 + SA2 \leqq -4$, both the axes are determined to exhibit hyperopia.

(4) Correction of Astigmatic Component C

The difference between the far refractive power determination and the near refractive power determination at the respective astigmatic axes is calculated:

$$CF = F2 - N1$$

$$CN = N2 - F1$$

where with $CF \times CN > 0$ and $CF < CN$, the average of both is defined as the astigmatic refractive power:

$$C = (CF + CN)/2$$

If no determination can be made through the aforementioned processing, this situation is determined to be indeterminate and thus an error, or the measurement is performed again.

Finally, all of the resulting determinations are checked with each other for consistency (S440). For example, the consistency with the rough determination processing and the consistency between the result from the hyperopia and myopia determination processing and the result of the refractive power determination processing are examined. When the data is inconsistent in the examination, the server 12 acknowledges an error and terminates the processing.

Through the processing described above, the astigmatic axis angle of the subject and the refractive powers at the astigmatic axis angle and at an angle orthogonal thereto are obtained.

As an additional function, this preferred embodiment also creates an optical eyeball model for simulating the eye of the subject in accordance with the aforementioned eye examination results to determine the lens power which is suitable for the eye of the subject.

To this end, a start eyeball model is selected in accordance with the age of the subject and an approximate refractive power (S500). Then, the focusing capability at the accommodation midpoint is evaluated and the optical system auto-design processing is performed to implement the best focusing condition, thereby constructing the optical eyeball model at the accommodation midpoint (S501).

Subsequently, the server 12 checks the model for validity at an accommodation limit (on the near point side) (S502). If the focusing condition is not sufficient, the flow returns to S501. This check for validity is performed to increase (UP) the eyeball refraction by the amount of accommodation provided by the human eye and to confirm through the optical system auto-design operation that the focusing is in a good condition. Here, to increase (UP) in the eyeball refraction by the amount of the accommodation is as follows.

With the far point distance being about 1 m (−1.0 D) and the near point distance being about 25 cm (−4.0 D), the position of the accommodation midpoint is about 40 cm (−2.5 D), in the case of which an UP in eyeball refraction corresponding to a correction of −1.5 D is required on the near point side as compared to at the accommodation midpoint position. The optical dimensions are varied as described below to carry out the optical system auto-design in order to provide an enhanced eyeball refraction corresponding to this −1.5 D. That is, the optical dimensions of the optical eyeball model are multiplied by $(1+\alpha \times b/a)$. The boundary conditions for the optical system auto-design are controlled. Meanwhile, a plurality of beams of light from an infinitesimal point object located at the near point distance of about 25 cm are allowed to enter the pupil of the optical eyeball model of a diameter (e.g., $\Phi=3$ mm) at various heights of incidence. The beams of light are traced such that the beams are focused at one point on the retina. When this results in a condition in which the beams are focused on one point, it is determined that the optical model has been successfully simulated at the accommodation limit, and thus, that the optical eyeball model of the subject is valid at the accommodation midpoint.

Subsequently, the server 12 checks the model for validity at an accommodation limit (on the far point side) (S504). If the focusing condition is not sufficient, the flow returns to S501. This check for validity is performed to decrease (DOWN) the eyeball refraction by the amount of accommodation provided by the human eye and to confirm through the optical system auto-design operation that the focusing is in good condition. Here, to decrease (DOWN) in the eyeball refraction by the amount of the accommodation is as follows.

With the far point distance being about 1 m (−1.0 D) and the near point distance being about 25 cm (−4.0 D), the position of the accommodation midpoint is about 40 cm (−2.5 D), in the case of which a DOWN in eyeball refraction corresponding to a correction of +1.5 D is required on the far point side as compared to at the accommodation midpoint position. The optical dimensions are varied as described below to perform the optical system auto-design in order to provide a reduced eyeball refraction corresponding to this +1.5 D. That is, the optical dimensions of the optical eyeball model are multiplied by $(1-\alpha \times b/a)$. The boundary conditions for the optical system auto-design are controlled. Meanwhile, a plurality of beams of light from an infinitesimal point object located at the far point distance of 1 m are allowed to enter the pupil of the optical eyeball model of a diameter (e.g., $\Phi=3$ mm) at various heights of incidence. The beams of light are traced such that the beams are focused at one point on the retina. When this results in a condition in which the beams are focused on one point, it is determined that the optical model has been successfully simulated at the accommodation limit, and thus, that the optical eyeball model of the subject is valid at the accommodation midpoint.

Furthermore, the model is checked for validity outside the accommodation range on the far point and near point sides, i.e., outside the accommodation range of the eyeball (S506). If there is an inconsistency, the flow returns to S501.

Then, the accommodation range of optical dimensions of the eyeball is finally determined to thereby determine the optical eyeball model (S508). The optical eyeball model at the position of the accommodation midpoint and the accommodation range of optical dimensions are finally determined as follows.

The processing for checking for validity of the optical eyeball model at the accommodation limits (on the near point and far point sides) is performed as described above. This allows for determining the optical eyeball model of the subject at the accommodation midpoint to be valid, which results from the optical eyeball model construction processing at the accommodation midpoint. The range of variations of the optical dimensions at the accommodation limits (especially the range of variations in the thickness, the front radii of curvature and the rear radii of curvature of the crystalline lens when reduced or increased in thickness) is determined through the processing for checking the optical eyeball model for validity at the accommodation limits on the near point side and the processing for checking the optical eyeball model for validity at the accommodation limit on the far point side.

With these parameters determined, the accommodation function of the eye can be simulated according to object distances.

Then, the focusing capabilities of the subject with naked eye condition that involve accommodation at the three distances are calculated and verified (S510). As in the processing for checking the optical eyeball model for validity at the accommodation limits (on the near point and far point sides), the amount of increase (UP) or decrease (DOWN) in the eyeball refraction at the accommodation midpoint is determined according to the distance of the object. While the boundary conditions for the optical system auto-design are being controlled, the optical system auto-design is performed. The optical dimensions determined in this manner represent the state of the eye when the focus of its eyeball virtually accommodated. The calculation is repeated until no improved focusing condition is achieved to get the final optical dimensions under the best focusing condition at the object distance.

To evaluate the focusing capability, several hundred beams of light from an infinitesimal point object located at a specific distance are uniformly distributed and entered at various heights of incidence into the pupil of the optical eyeball model having a diameter (e.g., $\Phi=3$ mm). The beams of light are traced so as to calculate at which point the beams are focused on the retina. To evaluate the degree of defocusing, a two-dimensional Fourier transform is performed on the intensity distribution of a point image on the retina, thereby calculating the spatial frequency characteristics (OTF) for assessment of the image.

The three distances are selected in the range of practical distances wearing eyeglasses which may possibly provide a significantly varied view. For example, they are about 0.3 m (near distance), about 0.5 m to about 0.6 m (intermediate distance), and about 5 m (far distance).

When the object is located at a farther distance than at the far point, it is determined that the crystalline lens cannot be further reduced in thickness, and thus, the focusing capability is checked with the accommodation at the far point distance. When the object is located at a nearer distance than at the near point, it is determined that the crystalline lens cannot be further increased in thickness, and thus, the focusing capability is checked with the accommodation at the near point distance. When the object is located at an intermediate distance between the near point and the far point, the eyeball refraction is varied by the amount of accommodation from the midpoint to check the focusing capability.

Then, the focusing capability that involves the accommodation at the three distances is calculated for evaluation after being corrected using eyeglasses or contact lenses (S512). That is, an actual eyeglass lens (where a radii of curvature of the lens at the front face and the rear face and a glass refractive index are known) is placed in front of the optical eyeball model. Then, the same calculation is conducted as in the focusing capability calculation processing with the naked eye. A suitable virtual lens is determined in accordance with the approximate lens power and the wearing conditions to perform an optical simulation regarding the focusing capability with the eyeglasses or contact lenses being worn.

When the balance of sharpness scores at the three distances is not sufficient, the lens power is slightly varied and the optical simulation is performed again (S514).

Then, the optical dimensions of the eye are varied within the range of accommodation to create a condition for the best focusing capability and then calculate the sharpness scores at that time.

The sharpness scores are calculated through the evaluation of the focusing condition. Several hundred beams of light from an infinitesimal point object located at a specific distance are uniformly distributed and entered into the pupil of the optical eyeball model having a diameter (e.g., $\Phi=3$ mm). The beams of light are traced so as to calculate at which point the beams are focused on the retina. The value obtained through the two-dimensional Fourier transform performed on the intensity distribution of the point image is defined as the spatial frequency characteristics (OTF). Examining how the intensity is distributed on the retina makes it possible to evaluate the degree of defocusing. The spatial frequency is a value to represent a fineness of a stripe pattern, and is defined by the number of stripes per unit length. For a visual system, it is represented by the number of stripes per one degree of visual angle. For example, assuming stripes are spaced at intervals of w (degree), the spatial frequency is $u=1/w$ (cycles/deg).

The value w used for evaluation of defocusing is determined according to the resolution of the retina, and the resulting value u is used to calculate the sharpness score.

Then, a recommended lens is finally determined (S516), and video images of views at the three distances are created before and after the correction using the recommended lens for display (S518). To this end, images at the three distances which have been photographed with high resolution are prepared, and N by N-size smoothing filter processing is performed pixel by pixel on these images and thereby blurred. The degree of blurring can be adjusted using the value N (at least 3), the filter weight, and the number of repetitions of the processing. The spatial frequency analysis is performed on the filtered images to determine the degree of defocusing to be associated with the aforementioned sharpness score.

Images corresponding to several sharpness scores are prepared, or alternatively, a score value is calculated which corresponds to an image obtained by performing a cycle of particular smoothing filter processing on the prepared images. A score value determined by calculating a sharpness score would be used to directly retrieve the corresponding image for display, or an image resulting from the filtering is made consistent with its sharpness score for display.

Alternatively, the lens may also be changed to create the video image at the three distances for display. That is, the lens power is changed to perform the optical simulation with an eyeglass or contact lens being worn. Then, the optical dimensions are changed within the range of accommodation of the eyeball to create the condition of the best focusing capability. And, in addition, the view images are created using the sharpness score obtained at that time.

The system described above allows the user to link his terminal to the optometric apparatus via a network, thereby performing a subjective eye examination and facilitating selection of eyeglasses or lenses suitable for the subject.

The aforementioned preferred embodiment is adapted such that the subject is linked to the eye examination server using a WWW browser to perform an eye examination. However, the present invention is not limited thereto. It is also acceptable that the aforementioned applications including the test symbols are downloaded into the user terminal for execution. The aforementioned applications including the test symbols may be not only downloaded from the eye examination server but also provided using a distributable storage medium such as CD-ROMs.

In this preferred embodiment, for determining astigmatic axes, the first astigmatic axis determination chart which includes test symbols with straight lines oriented at angles of about 45 degrees, about 90 degrees, about 135 degrees, and about 180 degrees, respectively, and the second astigmatic axis determination chart which includes test symbols with straight lines oriented at angles of about 23 degrees, about 68 degrees, about 113 degrees, and about 158 degrees, which equally divide the aforementioned orientations are used such that the subject is prompted to select test symbols in increments of about 23 degrees. However, the present invention is not limited thereto. Furthermore, a second astigmatic axis determination which includes a combination of four test symbols each oriented in either one of the orientations that divide into three equal parts the four orientations in the first astigmatic axis determination chart and a third astigmatic axis determination chart which includes four test symbols each oriented in either one of the orientations that divide into three equal parts the four orientations in the first astigmatic axis determination chart, that are not included in the second astigmatic axis determination chart may be used so that the subject is prompted to select test symbols in increments of about 15 degrees for determining the astigmatic axis in smaller increments. To permit the subject to easily select test symbols viewed with greater contrast, each astigmatic axis determination chart is configured to include four test symbols which have straight lines orthogonal to each other. When the astigmatic axis angle is not determined in the first, second, and third astigmatic axis determination charts, a fourth astigmatic axis determination chart may also be displayed for selection, which includes a combination of the test symbols selected by the subject in the first, second, and third astigmatic axis determination charts. If the two symbols are allowed to be selected in each of the first, second, and third astigmatic axis determination charts, a maximum number of six test symbols may be selected. In the case of displaying the fourth astigmatic axis determination chart, four of the test symbols having the adjacent angles are selected to create the astigmatic axis determination chart. This allows for determining the astigmatic axis angle with twice the resolution of the test symbols provided in increments of about 15 degrees, thereby determining the astigmatic axis angle with further improved accuracy.

In order to determine a test symbol having a size that is suitable for the subject, this preferred embodiment first performs the rough determination processing to determine a rough view. However, the order in which the rough determination is performed is not limited thereto. The rough determination may be performed, as appropriate, before the processing which requires determination of a size of a test symbol. Furthermore, if the subject is prompted to move close enough to the screen as at a distance where the subject can recognize the straight lines in the astigmatic axis determination processing or in the hyperopia and myopia determination processing, and the test symbols having an entire range of sizes are displayed in the refractive power determination processing, the rough determination processing may not be necessarily performed.

In the aforementioned preferred embodiment, the astigmatic axis determination processing, the hyperopia and myopia determination processing, and the refractive power determination processing have been performed as a series of steps. However, as used herein, the astigmatic axis determination processing, the hyperopia and myopia determination processing, and the refractive power determination processing may also be used separately, thereby also providing their respective unique effects as described above.

According to preferred embodiments of the present invention, it is possible to provide an optometric method which enables the determinations of astigmatic axis angles, of hyperopia or myopia, and of myopic, hyperopic, and astigmatic refractive powers without being affected by a subject's subjective viewpoint or the determination environment. The method can also be applicable to a wide range of refractive powers.

While the present invention has been described with respect to preferred embodiments, it will be apparent to those skilled in the art that the disclosed invention may be modified in numerous ways and may assume many embodiments other than those specifically set out and described above. Accordingly, it is intended by the appended claims to cover all modifications of the present invention that fall within the true spirit and scope of the invention.

The invention claimed is:

1. An optometric apparatus which performs a subjective eye examination by prompting a subject to view test symbols displayed on display means by one of the right and left eyes at a time and then obtaining a result of viewing by the subject, the optometric apparatus comprising:

astigmatic axis angle determination means for displaying test symbols for determining an astigmatic axis angle and then obtaining a result of viewing by the subject to determine the astigmatic axis angle;

hyperopia and myopia determination means for displaying test symbols for determining hyperopia or myopia in two orthogonal orientations selected in accordance with the determined astigmatic axis angle, and then obtaining a result of viewing by the subject to determine hyperopia or myopia at the determined astigmatic axis angle and at an angle orthogonal thereto; and refractive power determination means for displaying test symbols for determining a refractive power in two orthogonal orientations selected in accordance with the determined astigmatic axis angle, and then obtaining a result of viewing by the subject to determine refractive powers at the determined astigmatic axis angle and at an angle orthogonal thereto; wherein the hyperopia and myopia determination means comprises: means for displaying a first hyperopia and myopia determination chart having a red-based color background area and a blue-based color background area, in both of the areas black-based color straight lines are drawn in one of the two selected orthogonal orientations; means for prompting the subject to select the area which provides a clearer appearance of the straight lines to the subject in the displayed first hyperopia and myopia determination chart; means for displaying a second hyperopia and myopia determination chart having a red-based color background area and a blue-based color background area, in both of the areas black-based color straight lines are drawn in the other of the two selected orthogonal orientations; means for prompting the subject to select the area which provides a clearer appearance of the straight lines to the subject in the displayed second hyperopia and myopia determination chart; means for determining hyperopia and myopia at the determined astigmatic axis angle and at an angle orthogonal thereto in accordance with a result selected in the first hyperopia and myopia determination chart and a result selected in the second hyperopia and myopia determination chart.

2. The optometric apparatus according to claim 1, wherein the hyperopia and myopia determination means includes the hyperopia and myopia determination chart in which the blue-based color area has a lower brightness than that of the red-based color area.

3. The optometric apparatus according to claim 2, wherein the hyperopia and myopia determination means limits the time of displaying each of the hyperopia and myopia determination charts.

4. The optometric apparatus according to claim 1, comprising: rough determination means including means for displaying a rough determination chart in which test symbols having no directivity are varied in size in a stepwise manner and means for prompting the subject to select the smallest viewable test symbol in the displayed rough determination chart to determine a subject's rough view; wherein
the hyperopia and myopia determination means has means for adjusting the width and intervals of the straight lines drawn in each of the hyperopia and myopia determination charts displayed in accordance with the rough view determined.

5. An optometric apparatus which performs a subjective eye examination by prompting a subject to view test symbols displayed on display means by one of the right and left eyes at a time and then obtaining a result of viewing by the subject, the optometric apparatus comprising:
astigmatic axis angle determination means for displaying test symbols for determining an astigmatic axis angle and then obtaining a result of viewing by the subject to determine the astigmatic axis angle;
hyperopia and myopia determination means for displaying test symbols for determining hyperopia or myopia in two orthogonal orientations selected in accordance with the determined astigmatic axis angle, and then obtaining a result of viewing by the subject to determine hyperopia or myopia at the determined astigmatic axis angle and at an angle orthogonal thereto; and
refractive power determination means for displaying test symbols for determining a refractive power in two orthogonal orientations selected in accordance with the determined astigmatic axis angle, and then obtaining a result of viewing by the subject to determine refractive powers at the determined astigmatic axis angle and at an angle orthogonal thereto; wherein
the hyperopia and myopia determination means includes:
means for displaying a first hyperopia and myopia determination chart having a red-based color background area and a blue-based color background area, in both of the areas black-based color straight lines are drawn in one of the two selected orthogonal orientations; means for prompting the subject to select the area which provides a clearer appearance of the straight lines to the subject in the displayed first hyperopia and myopia determination chart; means for displaying a second hyperopia and myopia determination chart having a red-based color background area and a blue-based color background area, in both of the areas black-based color straight lines are drawn in the other of the two selected orthogonal orientations; means for prompting the subject to select the area which provides a clearer appearance of the straight lines to the subject in the displayed second hyperopia and myopia determination chart; means for displaying a third hyperopia and myopia determination chart having a red-based color background area in which black-based color straight lines are drawn in the one of the two selected orthogonal orientations and a blue-based color background area in which black-based color straight lines are drawn in the other of the two selected orthogonal orientations; means for prompting the subject to select the area which provides a clearer appearance of the straight lines to the subject in the displayed third hyperopia and myopia determination chart; means for displaying a fourth hyperopia and myopia determination chart having a red-based color background area in which black-based color straight lines are drawn in the other of the two selected orthogonal orientations and a blue-based color background area in which black-based color straight lines are drawn in the one of the two selected orthogonal orientations; means for prompting the subject to select the area which provides a clearer appearance of the straight lines to the subject in the displayed fourth hyperopia and myopia determination chart; and means for determining hyperopia and myopia at the determined astigmatic axis angle and at an angle orthogonal thereto in accordance with a result selected in the first hyperopia and myopia determination chart, a result selected in the second hyperopia and myopia determination chart, a result selected in the third hyperopia and myopia determination chart, and a result selected in the fourth hyperopia and myopia determination chart.

6. The optometric apparatus according to claim 5, wherein the hyperopia and myopia determination means includes the hyperopia and myopia determination chart in which the blue-based color area has a lower brightness than that of the red-based color area.

7. The optometric apparatus according to claim 6, wherein the hyperopia and myopia determination means limits the time of displaying each of the hyperopia and myopia determination charts.

8. The optometric apparatus according to claim 5, comprising: rough determination means including means for displaying a rough determination chart in which test symbols having no directivity are varied in size in a stepwise manner and means for prompting the subject to select the smallest viewable test symbol in the displayed rough determination chart to determine a subject's rough view; wherein
the hyperopia and myopia determination means has means for adjusting the width and intervals of the straight lines drawn in each of the hyperopia and myopia determination charts displayed in accordance with the rough view determined.

9. A lens power determination method for performing a subjective eye examination by prompting a subject to view test symbols displayed on display means by one of the right and left eyes at a time and then obtaining a result of viewing by the subject, the method comprising the steps of:

displaying test symbols for determining an astigmatic axis angle and then obtaining a result of viewing by the subject to determine the astigmatic axis angle;

displaying test symbols for determining hyperopia or myopia in two orthogonal orientations selected in accordance with the determined astigmatic axis angle, and then obtaining a result of viewing by the subject to determine hyperopia or myopia at the determined astigmatic axis angle and at an angle orthogonal thereto; and displaying test symbols for determining a refractive power in two orthogonal orientations selected in accordance with the determined astigmatic axis angle, and then obtaining a result of viewing by the subject to determine a refractive power at the determined astigmatic axis angle and at an angle orthogonal thereto; wherein the step of determining hyperopia and myopia comprises the steps of: displaying a first hyperopia and myopia determination chart having a red-based color background area and a blue-based color background area, in both of the areas black-based color straight lines are drawn in one of the two selected orthogonal orientations; prompting the subject to select the area which provides a clearer appearance of the straight lines to the subject in the displayed first hyperopia and myopia determination chart; displaying a second hyperopia and myopia determination chart having a red-based color background area and a blue-based color background area, in both of the areas black-based color straight lines are drawn in the other of the two selected orthogonal orientations; prompting the subject to select the area which provides a clearer appearance of the straight lines to the subject in the displayed second hyperopia and myopia determination chart; displaying a third hyperopia and myopia determination chart having a red-based color background area in which black-based color straight lines are drawn in the one of the two selected orthogonal orientations and a blue-based color background area in which black-based color straight lines are drawn in the other of the two selected orthogonal orientations in; prompting the subject to select the area which provides a clearer appearance of the straight lines to the subject in the displayed third hyperopia and myopia determination chart; displaying a fourth hyperopia and myopia determination chart having a red-based color background area in which black-based color straight lines are drawn in the other of the two selected orthogonal orientations and a blue-based color background area in which black-based color straight lines are drawn in the one of the two selected orthogonal orientations; prompting the subject to select the area which provides a clearer appearance of the straight lines to the subject in the displayed fourth hyperopia and myopia determination chart; and determining hyperopia and myopia at the determined astigmatic axis angle and at an angle orthogonal thereto in accordance with a result selected in the first hyperopia and myopia determination chart, a result selected in the second hyperopia and myopia determination chart, a result selected in the third hyperopia and myopia determination chart, and a result selected in the fourth hyperopia and myopia determination chart.

10. The lens power determination method according to claim 9, wherein the step of determining a refractive power comprises the steps of: sequentially displaying a plurality of refractive power determination charts which have a combination of test symbols having a certain number of straight lines drawn in parallel in the two selected orthogonal orientations in which the step difference in size is two or more; prompting the subject to select the smallest viewable test symbol in each of the displayed refractive power determination charts; and determining refractive powers at the determined astigmatic axis angle and at an angle orthogonal thereto in accordance with the test symbols selected in each of the refractive power determination charts.

* * * * *